(12) United States Patent
Axten et al.

(10) Patent No.: US 7,618,959 B2
(45) Date of Patent: Nov. 17, 2009

(54) ANTIBACTERIAL AGENTS

(75) Inventors: Jeffrey Michael Axten, Collegeville, PA (US); Timothy Francis Gallagher, Collegeville, PA (US); William Henry Miller, Collegeville, PA (US); Mark Andrew Seefeld, Collegeville, PA (US)

(73) Assignee: SmithKlineBeecham Corp, Philadelphia, PA (US)

(*) Notice: Subject to any disclaimer, the term of this patent is extended or adjusted under 35 U.S.C. 154(b) by 565 days.

(21) Appl. No.: 10/533,501

(22) PCT Filed: Nov. 4, 2003

(86) PCT No.: PCT/US03/35206

§ 371 (c)(1),
(2), (4) Date: May 2, 2005

(87) PCT Pub. No.: WO2004/041210

PCT Pub. Date: May 21, 2004

(65) Prior Publication Data

US 2007/0004710 A1  Jan. 4, 2007

Related U.S. Application Data

(60) Provisional application No. 60/423,872, filed on Nov. 5, 2002.

(51) Int. Cl.
C07D 513/04 (2006.01)
A61K 31/542 (2006.01)

(52) U.S. Cl. ...................... 514/224.2; 544/48

(58) Field of Classification Search .............. 544/48; 514/224.2
See application file for complete search history.

(56) References Cited

U.S. PATENT DOCUMENTS

| | | | |
|---|---|---|---|
| 5,633,270 A | 5/1997 | Dubroeucq et al. | |
| 5,670,527 A | 9/1997 | Garigipati et al. | |
| 5,705,646 A | 1/1998 | Bright et al. | |
| 5,707,987 A | 1/1998 | Nakagawa et al. | |
| 5,707,991 A | 1/1998 | Capet et al. | |
| 5,843,957 A | 12/1998 | Muraoka et al. | |
| 5,866,562 A | 2/1999 | Seidel et al. | |
| 5,958,948 A | 9/1999 | Bright et al. | |
| 5,969,184 A | 10/1999 | Adams et al. | |
| 6,150,557 A | 11/2000 | Adams et al. | |
| 6,194,413 B1 | 2/2001 | Bhatnagar et al. | 514/252.11 |
| 6,211,198 B1 | 4/2001 | Gluchowski et al. | |
| 6,300,500 B1 | 10/2001 | Muraoka et al. | |
| 6,323,373 B1 | 11/2001 | Spreitzer et al. | |
| 6,346,622 B1 | 2/2002 | Lubisch et al. | |
| 6,403,610 B1 | 6/2002 | Malleron et al. | 514/314 |
| 6,414,157 B1 | 7/2002 | Lubisch et al. | |
| 6,420,381 B1 | 7/2002 | Muraoka et al. | |
| 6,509,507 B2 | 1/2003 | Spreitzer et al. | |
| 6,602,882 B1 | 8/2003 | Davies et al. | 514/300 |
| 6,602,884 B2 | 8/2003 | Bacque et al. | 514/314 |
| 6,603,005 B2 | 8/2003 | Bacque et al. | 546/176 |
| 6,642,228 B1 | 11/2003 | Hayashi et al. | |
| 6,803,369 B1 | 10/2004 | Erskine et al. | 514/253.06 |
| 6,815,547 B2 | 11/2004 | Bacque et al. | 546/174 |
| 6,841,562 B2 | 1/2005 | Bacque et al. | 514/314 |
| 6,903,217 B2 | 6/2005 | Bacque et al. | 546/180 |
| 6,911,442 B1 | 6/2005 | Davies et al. | 514/230.5 |
| 6,962,917 B2 | 11/2005 | Davies et al. | 514/264.1 |
| 6,989,447 B2 | 1/2006 | Markwell et al. | 546/152 |
| 7,001,913 B1 | 2/2006 | Davies et al. | 514/300 |
| 2001/0006972 A1 | 7/2001 | Williams | |
| 2003/0203917 A1 | 10/2003 | Erskine et al. | 514/253.06 |
| 2003/0212084 A1 | 11/2003 | Hatton et al. | 514/266.22 |
| 2004/0053928 A1 | 3/2004 | Davies et al. | 514/248 |
| 2004/0077655 A1 | 4/2004 | Dartois et al. | 514/253.05 |
| 2004/0077656 A1 | 4/2004 | Markwell et al. | 514/253.05 |
| 2004/0087619 A1 | 5/2004 | Bacque et al. | 514/314 |
| 2004/0138219 A1 | 7/2004 | Davies et al. | 514/243 |
| 2004/0171620 A1 | 9/2004 | Brooks et al. | 514/248 |
| 2004/0198755 A1 | 10/2004 | Dartois et al. | 514/266.22 |
| 2004/0198756 A1 | 10/2004 | Davies et al. | 514/266.22 |
| 2004/0224946 A1 | 11/2004 | Bigot et al. | 514/227.8 |
| 2005/0032800 A1 | 2/2005 | Bigot et al. | 514/243 |
| 2005/0085494 A1 | 4/2005 | Daines et al. | 514/266.22 |
| 2005/0159411 A1 | 7/2005 | Daines et al. | 514/224.8 |
| 2006/0014749 A1 | 1/2006 | Davies et al. | 514/249 |
| 2006/0040925 A1 | 2/2006 | Davies et al. | 514/222.8 |
| 2006/0041123 A1 | 2/2006 | Axten et al. | 544/48 |
| 2006/0058287 A1 | 3/2006 | Axten et al. | 514/224.2 |
| 2006/0079546 A1 | 4/2006 | Davies et al. | 514/300 |
| 2006/0116512 A1 | 6/2006 | Axten et al. | 540/553 |
| 2006/0166477 A1 | 7/2006 | Axten et al. | 514/224.2 |
| 2006/0189601 A1 | 8/2006 | Hennessy et al. | 514/222.8 |
| 2006/0189604 A1 | 8/2006 | Axten et al. | 514/224.2 |

FOREIGN PATENT DOCUMENTS

| | | |
|---|---|---|
| CA | 2 328 720 A1 | 10/1999 |
| CA | 2 359 390 | 7/2000 |
| CA | 2500320 A1 | 4/2004 |
| DE | 19651439 A1 | 6/1998 |
| DE | 19746612 A1 | 4/1999 |
| DE | 19747063 A1 | 4/1999 |
| DE | 1990544 A1 | 7/2000 |
| EP | 524 595 A1 | 1/1993 |
| EP | 873 753 A1 | 10/1998 |
| EP | 1 293 503 A1 | 3/2003 |
| EP | 1218370 B1 | 12/2004 |
| FR | 2700166 A1 | 7/1994 |

(Continued)

OTHER PUBLICATIONS

Snyder et al., PubMed Abstract (J. Med. Liban 48(4): 208-214, Jul.-Aug. 2000.*

(Continued)

Primary Examiner—Kahsay T Habte
(74) Attorney, Agent, or Firm—Reid S. Willis; John Lemanowicz

(57) ABSTRACT

Quinoline and naphthyridine derivatives useful in the treatment of bacterial infections in mammals, particularly humans.

23 Claims, No Drawings

FOREIGN PATENT DOCUMENTS

| | | |
|---|---|---|
| FR | 2700168 A1 | 7/1994 |
| WO | WO 93/01170 A1 | 1/1993 |
| WO | WO 94/13661 A1 | 6/1994 |
| WO | WO 94/14433 A1 | 7/1994 |
| WO | WO 94/22829 A2 | 10/1994 |
| WO | WO 94/29300 A1 | 12/1994 |
| WO | WO 95/02591 A1 | 1/1995 |
| WO | WO 95/23150 A1 | 8/1995 |
| WO | WO 95/33727 A1 | 12/1995 |
| WO | WO 95/35310 A1 | 12/1995 |
| WO | WP 96/00212 A1 | 1/1996 |
| WO | WO 96/21452 A1 | 7/1996 |
| WO | WO 96/38445 A1 | 12/1996 |
| WO | WO97/17973 | 5/1997 |
| WO | WO 97/25045 A1 | 7/1997 |
| WO | WO 97/28799 A1 | 8/1997 |
| WO | WO 97/32583 A1 | 9/1997 |
| WO | WO 97/35855 A1 | 10/1997 |
| WO | WO 97/36587 A1 | 10/1997 |
| WO | WO 98/10653 A1 | 3/1998 |
| WO | WO 98/16230 A1 | 4/1998 |
| WO | WO 98/40386 A1 | 4/1998 |
| WO | WO 98/23615 A1 | 6/1998 |
| WO | WO 98/25617 A1 | 6/1998 |
| WO | WO 98/25896 A1 | 6/1998 |
| WO | WO 99/01130 A1 | 1/1999 |
| WO | WO 99/01437 A1 | 1/1999 |
| WO | WO 99/10329 A1 | 3/1999 |
| WO | WO 99/18942 A1 | 4/1999 |
| WO | WO 99/37635 | 7/1999 |
| WO | WO99/37635 A1 | 7/1999 |
| WO | WO 99/43659 A1 | 9/1999 |
| WO | WO 99/54320 A1 | 10/1999 |
| WO | WO 00/01670 A1 | 1/2000 |
| WO | WO 00/09505 A1 | 2/2000 |
| WO | WO 00/21948 | 4/2000 |
| WO | WO 00/21952 | 4/2000 |
| WO | WO 00/31063 A1 | 6/2000 |
| WO | WO 00/43383 | 7/2000 |
| WO | WO 00/64876 A1 | 11/2000 |
| WO | WO 00/64888 A1 | 11/2000 |
| WO | WO 00/66107 A1 | 11/2000 |
| WO | WO 00/78716 A1 | 12/2000 |
| WO | WO 00/78748 A1 | 12/2000 |
| WO | WO 01/07432 A2 | 2/2001 |
| WO | WO 01/07433 A2 | 2/2001 |
| WO | WO 01/25227 A2 | 4/2001 |
| WO | WO 01/55111 A1 | 8/2001 |
| WO | WO 01/81316 A2 | 11/2001 |
| WO | WO 01/87855 A1 | 11/2001 |
| WO | WO 02/00662 A2 | 1/2002 |
| WO | WO 02/08224 A1 | 1/2002 |
| WO | WO 02/24684 A1 | 3/2002 |
| WO | WO 02/40474 A2 | 5/2002 |
| WO | WO 02/50040 A1 | 6/2002 |
| WO | WO 02/50061 A1 | 6/2002 |
| WO | WO 02/056882 A1 | 7/2002 |
| WO | WO 02/072572 A1 | 9/2002 |
| WO | WO 02/096907 A1 | 12/2002 |
| WO | WO 03/010138 A2 | 2/2003 |
| WO | WO 03/064421 A1 | 8/2003 |
| WO | WO 03/064431 A2 | 8/2003 |
| WO | WO 03/087098 A1 | 10/2003 |
| WO | WO 2004/002490 A2 | 1/2004 |
| WO | WO 2004/002992 A1 | 1/2004 |
| WO | WO 2004/014361 A1 | 2/2004 |
| WO | WO 2004/024712 A1 | 3/2004 |
| WO | WO 2004/024713 A1 | 3/2004 |
| WO | WO 2004/035569 A2 | 4/2004 |
| WO | WO 2004/050036 A2 | 6/2004 |
| WO | WO 2004/058144 A2 | 7/2004 |
| WO | WO 2004/087145 A2 | 10/2004 |
| WO | WO 2004/087647 | 10/2004 |
| WO | WO 2004/089947 A2 | 10/2004 |
| WO | WO 2004/096982 A2 | 11/2004 |
| WO | WO2005/016916 | 2/2005 |

OTHER PUBLICATIONS

U.S. Appl. No. 09/889,820, Davies et al., filed Sep. 20, 2001, Quinoline Derivatives as Antibacterials, WO00/43383.

U.S. Appl. No. 10/868,351 (cont of U.S. Appl. No. 09/912,610, abandoned), Erskine et al., filed Jun. 15, 2004, Compounds and Methods for the Treatment of Disease.

U.S. Appl. No. 10/199,933, CIP of U.S. Appl. No. 09/912,610, Erskine et al., filed Jul. 19, 2002, Compounds and Methods for the Treatment of Disease.

U.S. Appl. No. 10/937,468, CIP of U.S. Appl. No. 09/912,610, Erskine et al., filed Sep. 9, 2004, Compounds and Methods for the Treatment of Disease.

* cited by examiner

ANTIBACTERIAL AGENTS

This application is a national stage entry of PCT/US2003/035206 filed Nov. 4, 2003, which claims the benefit of U.S. Provisional Application No. 60/423,872 filed Nov. 5, 2002.

FIELD OF THE INVENTION

This invention relates to novel compounds, compositions containing them and their use as antibacterials.

BACKGROUND OF THE INVENTION

The emergence of pathogens resistant to known antibiotic therapy is becoming a serious global healthcare problem (Chu, et al., (1996) *J. Med. Chem.*, 39: 3853-3874). Thus, there is a need to discover new broad spectrum antiobiotics useful in combating multidrug-resistant organisms. Importantly, it has now been discovered that certain compounds have antibacterial activity, and, therefore, may be useful for the treatment of bacterial infections in mammals, particularly in humans.

WO99/37635, WO00/21948, WO00/21952, WO00/43383, WO00/78748, WO01/07433, WO01/07432, WO01/25227, WO0208224, WO0224684, PCT/GB01/05653, PCT/GB01/05661 and WO02040474 disclose quinoline and naphthyridine derivatives having antibacterial activity.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also a method of treating bacterial infections in mammals, particularly in humans.

DETAILED DESCRIPTION OF THE INVENTION

This invention provides a compound of formula (I) or a pharmaceutically acceptable derivative thereof:

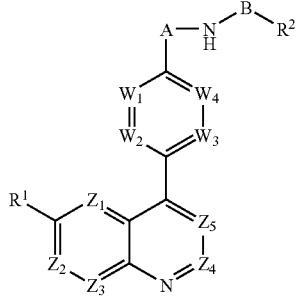

(I)

wherein:
one Of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;

$R^1$ and $R^{1a}$ are independently hydrogen; hydroxy; $(C_{1-6})$ alkoxy unsubstituted or substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$ alkylthio, heterocyclylthio, heterocyclyloxy, arylthio, aryloxy, acylthio, acyloxy or $(C_{1-6})$alkylsulphonyloxy; $(C_{1-6})$ alkoxy-substituted$(C_{1-6})$alkyl; halogen; $(C_{1-6})$alkyl; $(C_{1-6})$ alkylthio; trifluoromethyl; trifluoromethoxy; nitro; cyano; azido; acyl; acyloxy; acylthio; $(C_{1-6})$alkylsulphonyl; $(C_{1-6})$ alkylsulphoxide; arylsulphonyl; arylsulphoxide or an amino, piperidyl, guanidino or amidino group optionally N-substituted by one or two $(C_{1-6})$alkyl, acyl or $(C_{1-6})$ alkylsulphonyl groups;

provided that when $Z_1$, $Z_2$, $Z_3$, $Z_4$ and $Z_5$ are $C^{1a}$ or CH, then $R^1$ is not hydrogen;

$W_1$, $W_2$, $W_3$ and $W_4$ are each independently selected from N or $CR^3$;

each $R^3$ is independently selected from: hydrogen; hydroxy; halogen; trifluoromethyl; trifluoromethoxy; cyano; nitro; azido; acyl; acyloxy; acylthio; amino, mono- and di-$(C_{1-6})$ alkylamino; and substituted and unsubstituted $(C_{1-6})$ alkoxy, $(C_{1-6})$alkyl, $(C_{3-7})$cycloalkyl, aminocarbonyl, $(C_{1-6})$alkylthio, $(C_{1-6})$alkylsulphonyl, and $(C_{1-6})$alkylsulphoxide;

A is $(CRR)_n$;
B is $(CRR)_m$, $C=O$, or $SO_2$;
n is 1 or 2;
m is 1 or 2
provided that when n is 1, m is 2; when n is 2, m is 1; and when B is $C=O$ or $SO_2$ then n is 2;

each R is independently selected from: hydrogen; halogen; trifluoromethyl; trifluoromethoxy; cyano; nitro; azido; acyl; acyloxy; acylthio; amino, mono- and di-$(C_{1-6})$alkylamino; and substituted and unsubstituted $(C_{1-6})$alkoxy, $(C_{1-6})$alkyl, $(C_{3-7})$cycloalkyl, aminocarbonyl, $(C_{1-6})$alkylthio, $(C_{1-6})$alkylsulphonyl, and $(C_{1-6})$alkylsulphoxide;

$R^2$ is a substituted or unsubstituted bicyclic carbocyclic or heterocyclic ring system of formula (A):

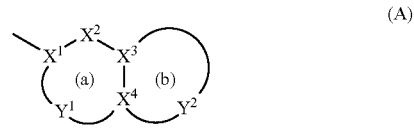

(A)

containing up to four heteroatoms in each ring in which ring (a) is aromatic and ring (b) is aromatic or non-aromatic;

$X^1$ is C;
$X^2$ is N, $NR^6$, O, $S(O)x$, CO, $CR^4$ or $CR^4R^5$;
$X^3$ and $X^4$ are each independently N or C;
$Y^1$ is a 1 to 2 atom linker group each atom of which is independently selected from N and $CR^4$;
$Y^2$ is a 2 to 6 atom linker group, each atom of $Y^2$ being independently selected from N, $NR^6$, O, $S(O)x$, CO, $CR^4$ and $CR^4R^5$;

each $R^4$ and $R^5$ is independently selected from: hydrogen; $(C_{1-4})$alkylthio; halo; carboxy$(C_{1-4})$alkyl; halo$(C_{1-4})$ alkoxy; halo$(C_{1-4})$alkyl; $(C_{1-4})$alkyl; $(C_{2-4})$alkenyl; $(C_{1-4})$ alkoxycarbonyl; formyl; $(C_{1-4})$alkylcarbonyl; $(C_{2-4})$alkenyloxycarbonyl; $(C_{2-4})$alkenylcarbonyl; $(C_{1-4})$ alkylcarbonyloxy; $(C_{1-4})$alkoxycarbonyl$(C_{1-4})$alkyl; hydroxy; hydroxy$(C_{1-4})$alkyl; mercapto$(C_{1-4})$alkyl; $(C_{1-4})$ alkoxy; nitro; cyano; carboxy; amino or aminocarbonyl is optionally substituted by $(C_{1-4})$alkoxycarbonyl, $(C_{1-4})$ alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; $(C_{2-6})$ alkenyl; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; aryl$(C_{1-4})$alkoxy; or $R^4$ and $R^5$ may together represent oxo;

each $R^6$ is independently hydrogen; trifluoromethyl; $(C_{1-4})$ alkyl unsubstituted or substituted by hydroxy, $(C_{1-6})$ alkoxy, $(C_{1-6})$alkylthio, halo or trifluoromethyl; $(C_{2-4})$alkenyl; aryl; aryl$(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$ alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; and each x is independently 0, 1, or 2; or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

The invention also provides a pharmaceutical composition, in particular for use in the treatment of bacterial infections in mammals, particularly humans, comprising a compound of formula (I), or a pharmaceutically acceptable derivative thereof, and a pharmaceutically acceptable carrier.

The invention further provides a method of treatment of bacterial infections in mammals, particularly in humans, which method comprises the administration to a mammal in need of such treatment an effective amount of a compound of formula (I), or a pharmaceutically acceptable derivative thereof.

Preferably $Z_5$ is CH or N, $Z_3$ is CH or CF and $Z_1$, $Z_2$ and $Z_4$ are each CH, or $Z_1$ is N, $Z_3$ is CH or CF and $Z_2$, $Z_4$ and $Z_5$ are each CH.

When $R^1$ or $R^{1a}$ is substituted alkoxy it is preferably $(C_{2-6})$ alkoxy substituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, amino $(C_{3-5})$alkyloxy, guanidino$(C_{3-5})$alkyloxy, piperidyl$(C_{3-5})$ alkyloxy, nitro or fluoro. More preferably $R^1$ and $R^{1a}$ are independently methoxy, amino$(C_{3-5})$alkyloxy or guanidino $(C_{3-5})$alkyloxy. Most preferably $R^1$ is methoxy and $R^{1a}$ is H or when $Z^3$ is $CR^{1a}$ it may be CF.

Preferably $W_1$-$W_4$ are independently $CR^3$; $W_1$, $W_3$ and $W_4$ are N and $W_2$ is $CR^3$; $W_2$ is N and $W_1$, $W_3$ and $W_4$ are independently $CR^3$; $W_3$ is N and $W_1$, $W_2$ and $W_4$ are independently $CR^3$; or $W_4$ is N and $W_1$-$W_3$ are independently $CR^3$.

Preferably $R^3$ is hydrogen, $(C_{1-6})$alkoxy, or $NH_2$.

Most preferably $R^3$ is hydrogen.

Preferably each R is independently selected from hydrogen, $(C_{1-6})$alkyl, $CONH_2$, COOH, hydroxy, halogen, and $(C_{1-6})$alkoxy.

Most preferably each R is hydrogen.

Preferably in the heterocyclic ring (A) $Y^2$ has 3-5 atoms, more preferably 4 atoms, including CH, $NR^6$, O or S bonded to $X^4$ and NHCO bonded via N to $X^3$, or O or NH bonded to $X^3$. Ring (a) is preferably substituted and unsubstituted phenyl and pyridine. Preferably ring (b) is substituted and unsubstituted pyridine, dioxane, piperidine, morpholin-3-one, thiomorpholin-3-one, oxazolidin-2-one, thiadiazole, and thiazepan-5-one. Examples of ring (A) groups include substituted or unsubstituted: 1,1,3-trioxo-1,2,3,4-tetrahydro 6-benzo[1,4]thiazin-3-one-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydro-benzo[b][1,4]thiazepine-7-yl, 5-oxo-2,3-dihydro-5H-thiazolo[3,2-a]pyrimidin-6-yl, benzo[1,3]dioxol-5-yl, 1H-pyrido[2,3-b][1,4]thiazin-2-one-7-yl (2-oxo-2,3-dihydro-1H-pyrido[2,3-b]thiazin-7-yl), 2,3-dihydro-1H-pyrido[2,3-b][1,4]thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4]oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 4H-pyrido[3,2-b][1,4]thiazin-3-one-6-yl, 4H-pyrido[3,2-b][1,4]oxazin-3-one-6-yl, 1,2,3,4-tetrahydro-[1,8]naphthyridine-7-yl, 1H-pyrido[3,2-b][1,4] thiazin-2-one-7-yl, and 6-fluoro-2,3-dihydrobenzo[1,4] dioxine-7-yl.

$R^4$ and $R^5$ are preferably independently selected from hydrogen, halo, hydroxy, $(C_{1-4})$alkoxy, trifluoromethoxy, nitro, cyano, aryl$(C_{1-4})$alkoxy and $(C_{1-4})$alkylsulphonyl. More preferably $R^5$ is hydrogen.

More preferably each $R^4$ is selected from hydrogen, chloro, fluoro, hydroxy, methoxy, trifluoromethoxy, benzyloxy, nitro, cyano and methylsulphonyl. Most preferably $R^4$ is selected from hydrogen, fluorine or nitro.

$R^6$ is preferably H if in ring (a) or in addition $(C_{1-4})$alkyl such as methyl or isopropyl when in ring (b). More preferably, in ring (b) $R^6$ is H when $NR^6$ is bonded to $X^3$ and $(C_{1-4})$alkyl when $NW^6$ is bonded to $X^5$.

Most preferred examples of $R^2$ are:
4H-benzo[1,4]thiazin-3-one-6-yl,
4H-pyrido[3,2-b][1,4]thiazin-3-one-6-yl,
4H-pyrido[3,2-b][1,4]oxazin-3-one-6-yl,
1,2,3,4-tetrahydro-[1,8]naphthyridine-7-yl,
1H-pyrido[3,2-b][1,4]thiazin-2-one-7-yl,
4H-benzo[1,4]oxazin-3-one-6-yl, and
6-fluoro-2,3-dihydrobenzo[1,4]dioxine-7-yl.

Preferred compounds of this invention are:
  6-({2-[4-(6-Methoxy-[1,5]naphthyridin-4-yl)phenyl] ethylamino}methyl)-4H-benzo[1,4]thiazin-3-one;
  6-({2-[4-(6-Methoxy-[1,5]naphthyridin-4-yl)phenyl] ethylamino}methyl)-4H-pyrido[3,2-b][1,4]thiazin-3-one;
  6-({2-[4-(6-Methoxy-[1,5]naphthyridin-4-yl)phenyl] ethylamino}methyl)-4H-pyrido[3,2-b][1,4]oxazin-3-one;
  3-Oxo-3,4-dihydro-2H-benzo[1,4]thiazine-6-sulfonic acid {2-[4-(6-methoxy-[1,5]naphthyridin-4-yl)phenyl] ethyl}amide;
  {2-[4-(6-Methoxy-[1,5]naphthyridin-4-yl)phenyl]ethyl} (5,6,7,8-tetrahydro[1,8]naphthyridin-2-ylmethyl)amine;
  6-{[4-(6-Methoxy-[1,5]naphthyridin-4-yl)benzylamino] methyl}-4H-benzo[1,4]thiazin-3-one;

7-({2-[4-(6-Methoxy-[1,5]naphthyridin-4-yl)phenyl]ethylamino}methyl)-1H-pyrido[3,2-b][1,4]thiazin-2-one;

6-{2-[4-(6-Methoxy-[1,5]naphthyridin-4-yl)benzylamino]ethyl}-4H-benzo[1,4]oxazin-3-one;

6-{2-[4-(6-Methoxy-[1,5]naphthyridin-4-yl)benzylamino]ethyl}-4H-benzo[1,4]thiazin-3-one;

(7-Fluoro-2,3-dihydrobenzo[1,4]dioxin-6-ylmethyl){2-[6-(6-methoxy[1,5]naphthyridin-4-yl)[1,2,4]triazin-3-yl]ethyl}amine;

6-({2-[4-(6-Methoxyquinolin-4-yl)phenyl]ethylamino}methyl)-4H-pyrido[3,2-b][1,4]oxazin-3-one;

6-({2-[4-(6,8-difluoroquinolin-4-yl)phenyl]ethylamino}methyl)-4H-pyrido[3,2-b][1,4]thiazin-3-one;

6-({2-[4-(8-Fluoro-6-methoxyquinolin-4-yl)phenyl]ethylamino}methyl)-4H-pyrido[3,2-b][1,4]thiazin-3-one;

6-({2-[6-(6-methoxy-[1,5]naphthyridin-4-yl)pyridin-3-yl]ethylamino}methyl)-4H-pyrido[3,2-b][1,4]thiazin-3-one;

6-({2-[5-(6-methoxy-[1,5]naphthyridin-4-yl)pyridin-2-yl]ethylamino}methyl)-4H-pyrido[3,2-b][1,4]thiazin-3-one;

6-({2-[6-(6-methoxy-[1,5]naphthyridin-4-yl)pyridin-3-yl]ethylamino}methyl)-4H-pyrido[3,2-b][1,4]oxazin-3-one;

N-(2,3-dihydro[1,4]dioxino[2,3-c]pyridin-7-ylmethyl)-2-{6-[6-(methyloxy)-1,5-naphthyridin-4-yl]-3-pyridinyl}ethanamine;

N-(2,3-dihydro[1,4]dioxino[2,3-c]pyridin-7-ylmethyl)-2-{5-[6-(methyloxy)-1,5-naphthyridin-4-yl]-2-pyridinyl}ethanamine;

N-(2-{6-[6-(methyloxy)-1,5-naphthyridin-4-yl]-3-pyridinyl}ethyl)-3-oxo-3,4-dihydro-2H-pyrido[3,2-b][1,4]thiazine-6-carboxamide; and N-(2-{5-[6-(methyloxy)-1,5-naphthyridin-4-yl]-2-pyridinyl}ethyl)-3-oxo-3,4-dihydro-2H-pyrido[3,2-b][1,4]thiazine-6-carboxamide;

or a pharmaceutically acceptable salt thereof.

Unless otherwise defined, the term $(C_{1-6})$alkyl when used alone or when forming part of other groups (such as the 'alkoxy' group) includes substituted or unsubstituted, straight or branched chain alkyl groups containing 1 to 6 carbon atoms. Examples of $(C_{1-6})$alkyl include methyl, ethyl, n-propyl, isopropyl, n-butyl, isobutyl and tert-butyl groups.

The term $(C_{2-6})$alkenyl means a substituted or unsubstituted alkyl group of 2 to 6 carbon atoms, wherein one carbon-carbon single bond is replaced by a carbon-carbon double bond. Examples of $(C_{2-6})$alkenyl include ethylene, 1-propene, 2-propene, 1-butene, 2-butene, isobutene and the several isomeric pentenes and hexenes. Both cis and trans isomers are included.

The term $(C_{3-7})$cycloalkyl refers to substituted or unsubstituted carbocyclic system of three to seven carbon atoms, which may contain up to two unsaturated carbon-carbon bonds. Examples of $(C_{3-7})$cycloalkyl include cyclopropyl, cyclobutyl, cyclopentyl, cyclopentenyl, cyclohexyl, cyclohexenyl, and cycloheptyl.

Unless otherwise defined, suitable substituents for any $(C_{1-6})$alkyl, $(C_{2-6})$alkenyl, and $(C_{3-7})$cycloalkyl groups includes up to three substituents selected from the group consisting of hydroxy, halogen, nitro, cyano, carboxy, amino, amidino, sulphonamido, unsubstituted $(C_{1-6})$alkoxy, trifluromethyl, acyloxy, quanidino, unsubstituted $(C_{3-7})$cycloalkyl, aryl, and heterocyclic.

Halo or halogen includes fluoro, chloro, bromo and iodo. Haloalkyl moieties include 1-3 halogen atoms.

Unless otherwise defined, the term "heterocyclic" as used herein includes optionally substituted aromatic and non-aromatic, single and fused, rings suitably containing up to four heteroatoms in each ring selected from oxygen, nitrogen and sulphur, which rings may be unsubstituted or C-substituted by, for example, up to three groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy $(C_{1-4})$alkyl; mercapto$(C_{1-4})$alkyl; $(C_{1-4})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl$(C_{1-4})$alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautomeric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl $(C_{1-4})$alkyl; hydroxy; hydroxy$(C_{1-4})$alkyl; mercapto$(C_{1-4})$alkyl; $(C_{1-4})$alkoxy.; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy The term "acyl" includes formyl and $(C_{1-6})$alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-tofuenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

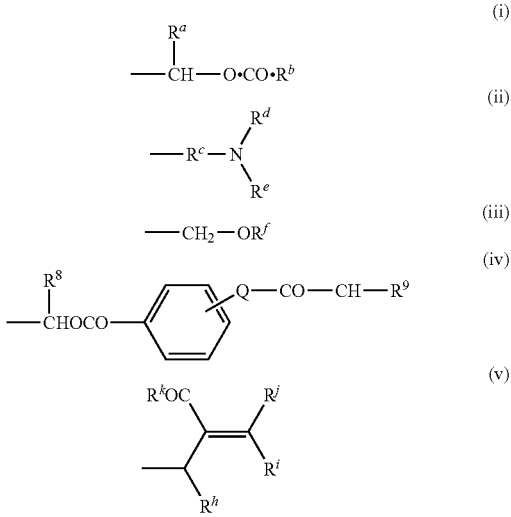

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

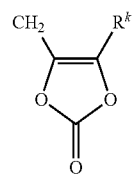

wherein $R^k$ is hydrogen, $(C_{1-6})$ alkyl or phenyl.

Certain of the above-mentioned compounds of formula (I) may exist in the form of optical isomers, e.g. diastereoisomers and mixtures of isomers in all ratios, e.g. racemic mixtures. The invention includes all such forms, in particular the pure isomeric forms. For examples the invention includes compound in which an A-B group CH(OH)—CH$_2$ is in either isomeric configuration the R-isomer is preferred. The different isomeric forms may be separated or resolved one from the other by conventional methods, or any given isomer may be obtained by conventional synthetic methods or by stereospecific or asymmetric syntheses.

The following examples illustrate the preparation of certain compounds of formula (I) and the activity of certain compounds of formula (I) against various bacterial organisms.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of the present invention were prepared by the methods illustrated in Schemes I-VI.

Scheme I

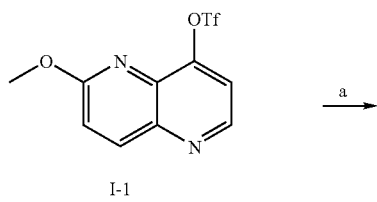

I-1

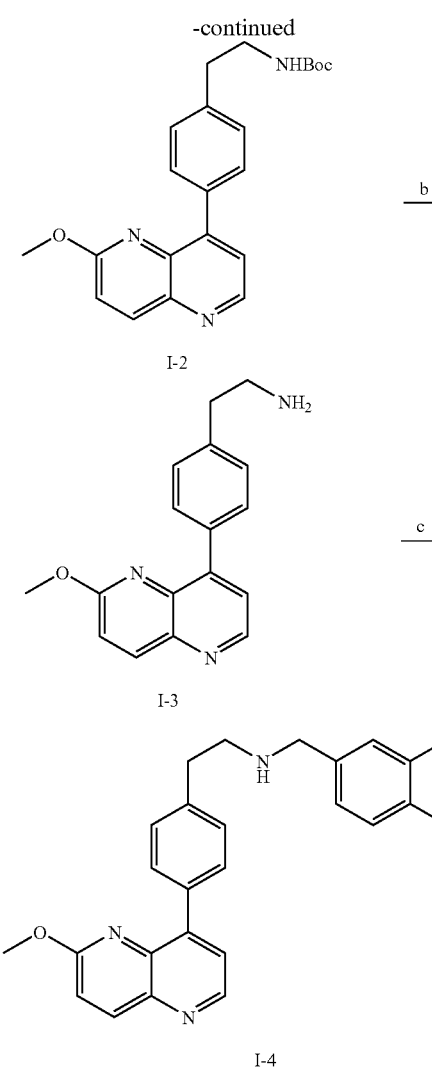

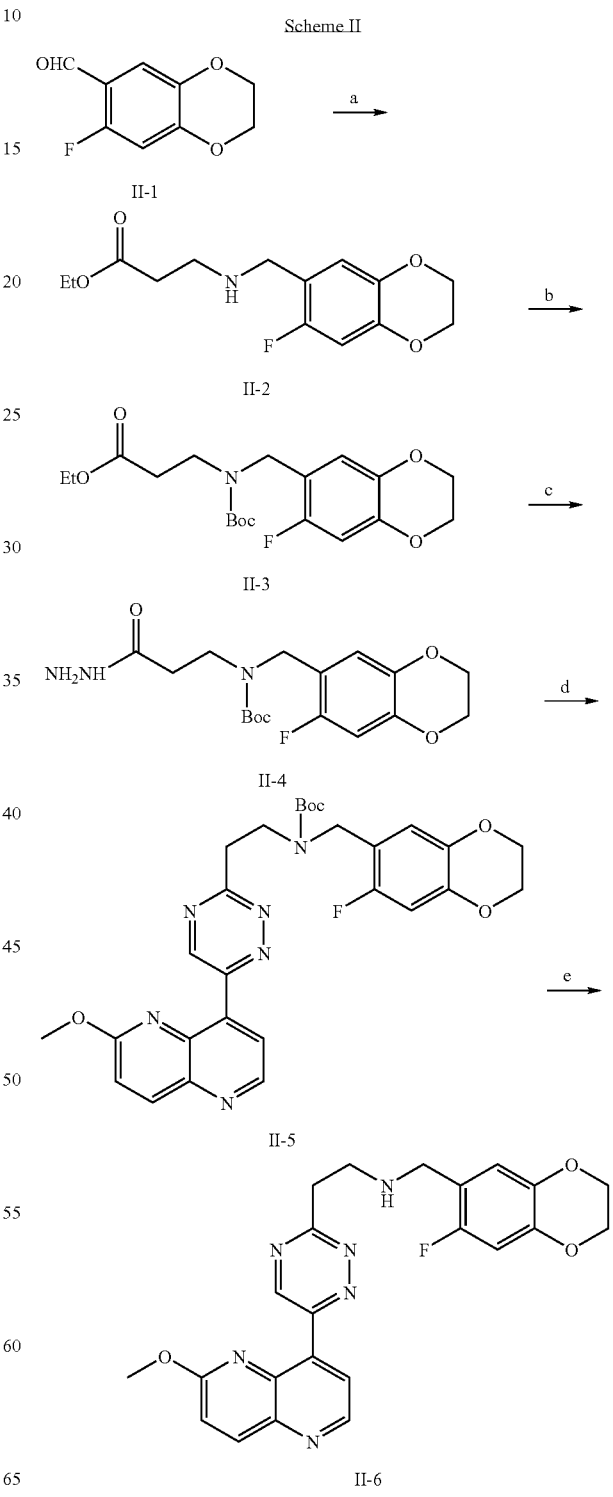

NaBH$_3$CN in solvent. Depending on whether acid neutralization is required, an added base, such as triethylamine (Et$_3$N), diisopropylethylamine ((i-Pr)$_2$NEt), or K$_2$CO$_3$, may be used. Many additional 5 methods for reductive aminations are known, and can be found in standard reference books, such as "Compendium of Organic Synthetic Methods", Vol. I-VI (published by Wiley-Interscience).

Reagents and conditions: (a) bis(pinacolato)diboron, dppf, Pdcl$_2$(dppf), KOAc, dioxane; then dppf, pdCl$_2$(dppf), K$_2$CO$_3$, [2-(4-bromophenyl)ethyl]carbamic acid tert-butyl ester (b) trifluoroacetic acid, CH$_2$Cl$_2$; (c) 3-oxo-3,4-dihydro-2H-benzol[1,4]thiazine-6-carboxaldehyde, CH$_2$Cl$_2$, EtOH; then NaBh$_4$, EtOH.

Triflate (I-1) is reacted under Suzuki coupling conditions in a one-pot procedure (Ishiyama, T.; Itoh, Y; Kitano, T.; Miyaura, N. Tetrahedron Lett. 1997, Vol. 38, No. 19, pp. 3447-3450) with an aromatic halide or aromatic triflate to afford I-2. Removal of the Boc protecting group is carried out under standard acidic conditions to give the free amine I-3. The use of protecting groups to mask reactive functionality is well-known to those of skill in the art, and other protecting groups are listed in standard reference volumes, such as Greene, "Protective Groups in Organic Synthesis" (published by Wiley-Interscience). The primary amine derivative is then converted to a secondary amine I-4 by reaction with an aldehyde and a suitable reducing agent. For example, 2-[4-(6-methoxy[1,5]naphthyridin-4-yl)phenyl]ethylamine is converted to an imine by reaction with an aldehyde in protic or aprotic solvents such as DMF, CH$_2$Cl$_2$, EtOH or CH$_3$CN. The imine is subsequently or simultaneously reacted with a suitable reducing agent such as NaBH$_4$, NaBH(OAc)$_3$ or Reagents and conditions: (a) α-alanine ethyl ester, Et₃N, DMF; then NaBH₄, EtOH; (b) di-tert-butyl dicarbonate, MeOH; (c) N₂H₄, EtOH; (d) 2-bromo-1-(6-methoxyl[1,5]naphthyridin-4-yl)ethanone, DMF; (e) trifluroacetic acid, CH₂Cl₂.

Aldehyde (II-1) is reacted with a primary amine to form an imine which can be reduced in situ to a secondary amine (II-2) by reaction with a suitable reducing agent. For example, β-alanine ethyl ester is converted to an imine by reaction with an aldehyde in protic or aprotic solvents such as DMAF, CH₂Cl₂, EtOH or CH₃CN. The imine is subsequently or simultaneously reacted with a suitable reducing agent such as NaBH₄, NaBH(OAc)₃ or NaBH₃CN in solvent. Depending on whether acid neutralization is required, an added base, such as triethylamine (Et₃N), diisopropylethylamine ((i-Pr)₂NEt), or K₂CO₃, may be used. Many additional methods for reductive aminations are known, and can be found in standard reference books, such as "Compendium of Organic Synthetic Methods", Vol. I-VI (published by Wiley-Interscience). The amine functionality is protected with a Boc protecting group. The use of protecting groups to mask reactive functionality is well-known to those of skill in the art, and other protecting groups are listed in standard reference volumes, such as Greene, "Protective Groups in Organic Synthesis" (published by Wiley-Interscience). The ethyl ester (II-3) is reacted with hydrazine to give the hydrazide II-4 which is subsequently reacted with an α-haloketone to afford the cyclocondensation product II-5. Removal of the Boc protecting group is carried out under standard acidic conditions to give the free amine II-6.

Scheme III

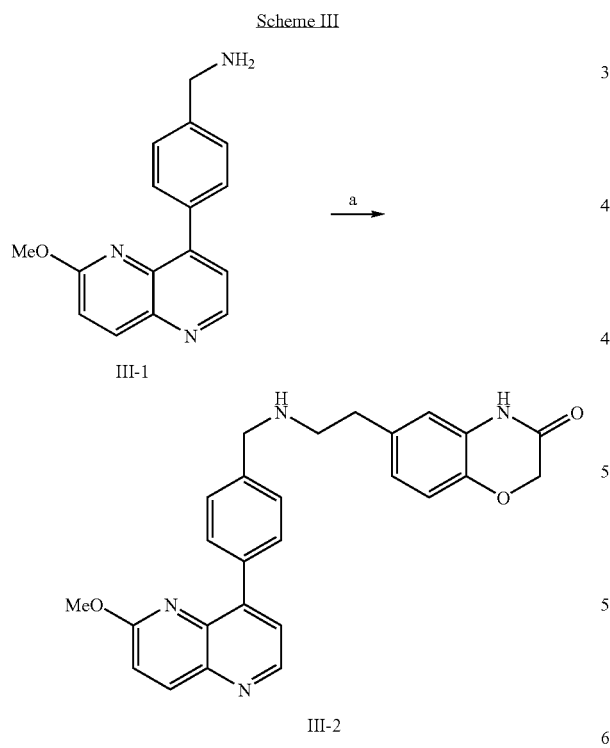

Reagents and conditions: (a) 6-(2-chloroethyl)-4H-benzo[1,4]oxazin-3-one, NaI, K₂CO₃, CH₃CN, 80° C.

Amine (III-1) is reacted with a primary alkyl halide or similar functionality, such as alkyl tosylates or alkyl mesylates, to form a secondary amine (III-2). For example, 6-(2-chloroethyl)-4H-benzo[1,4]oxazin-3-one is heated in protic or aprotic solvent such as DMF, CH₂Cl₂, EtOH or CH₃CN with a suitable amine using NaI as a halogen exchange catalyst. Depending on whether acid neutralization is required, an added base, such as triethylamine (Et₃N), diisopropylethylamine ((i-Pr)₂NEt), or K₂CO₃, may be used.

Scheme IV

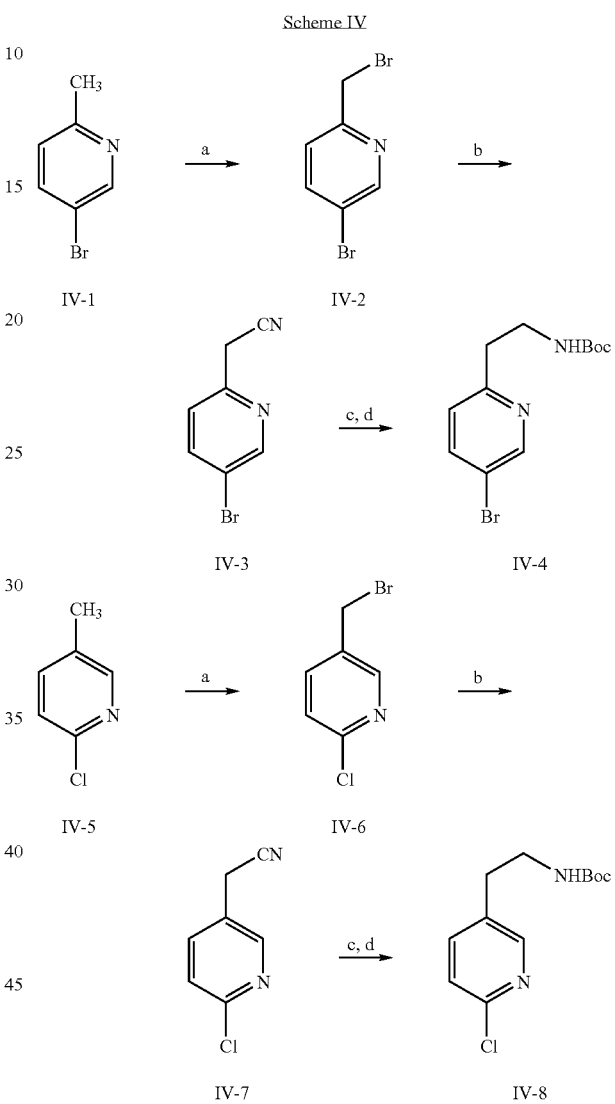

Reagents and conditions: (a) NBS, benzoyl peroxide, CCl₄, 70° C.; (b) KCN, EtOH, H₂O, 60° C.; (c) B₂H₆, THF, RT (d) (Boc)₂O, THF, RT.

Methyl pyridine (IV-1 or IV-4) is reacted under radical halogen generating conditions to afford the methyl bromide product (IV-2 or IV-6). Benzylic halogenation under radical conditions is well-known to those in the art. The methyl bromides (IV-2 or IV-6) are then treated with a cyano nucleophile in an appropriate solvent (eg, H₂O/MeOH, DMF) to give the nitrile products (IV-3 or IV-7) via a standard SN2 displacement chemistry which is exemplified in all introductory chemistry textbooks. Reduction of the nitrile functionality using a suitable reducing agent such as (LiAlH₄, B₂H₆, H₂-Pd/C, etc.) see ("Borane Reagents" Best Synthetic Methods, A. Pelter, K. Smith, H. C. Brown; Academic Press) provides a primary amine. The primary amine can be protected with a suitably reactive reagent such as (Boc)₂O, in situ to provide the carbamates (IV-4 or IV-8).

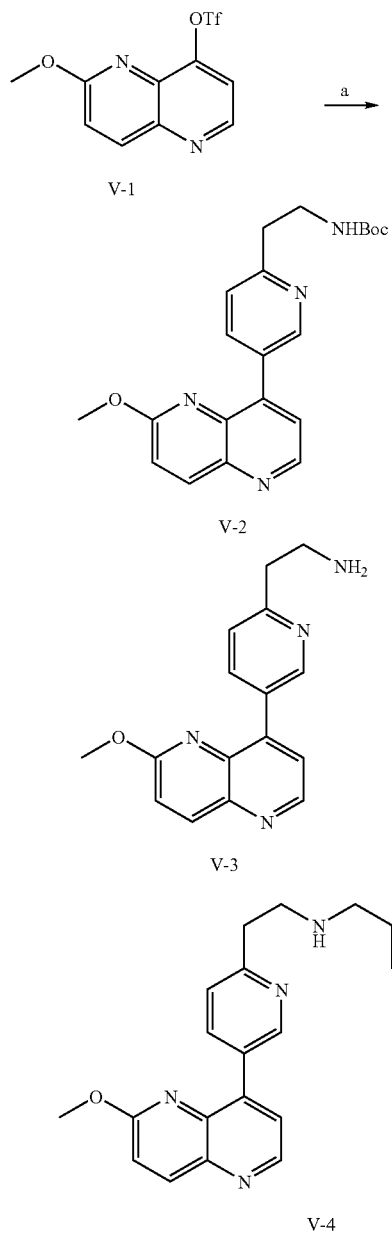

Reagents and conditions: (a) bis(pinacolato)diboron, dppf, PdCl₂(dppf), KOAc, dioxane, then dppf, PdCl₂(dppf, K₂CO₃, V-3; (b) HCl, dioxane; (c) 3-oxo-3,4-dihydro-2H-pyrido[1,4] thiazine-6-carboxaldehyde, CH₂Cl₂, EtOH; then NaBH₄, EtOH.

Triflate (V-1) is reacted under Suzuki coupling conditions in a one-pot procedure (Ishiyama, T.; Itoh, Y; Kitano, T.; Miyaura, N. Tetrahedron Lett. 1997, Vol. 38, No. 19, pp. 3447-3450) with an aromatic halide or aromatic triflate to afford V-2. Removal of the Boc protecting group is carried out under standard acidic conditions to give the free amine V-3. The use of protecting groups to mask reactive functionality is well-known to those of skill in the art, and other protecting groups are listed in standard reference volumes, such as Greene, "Protective Groups in Organic Synthesis" (published by Wiley-Interscience). The primary amine derivative is then converted to a secondary amine V-4 by reaction with an aldehyde and a suitable reducing agent. For example, 2-[4-(6-methoxy[1,5]naphthyridin-4-yl)phenyl]ethylamine is converted to an imine by reaction with an aldehyde in protic or aprotic solvents such as DMF, CH₂Cl₂, EtOH or CH₃CN. The imine is subsequently or simultaneously reacted with a suitable reducing agent such as NaBH₄, NaBH(OAc)₃ or NaBH₃CN in solvent. Depending on whether acid neutralization is required, an added base, such as triethylamine (Et₃N), diisopropylethylamine ((i-Pr)₂NEt), or K₂CO₃, may be used. Many additional methods for reductive aminations are known, and can be found in standard reference books, such as "Compendium of Organic Synthetic Methods", Vol. I-VI (published by Wiley-Interscience).

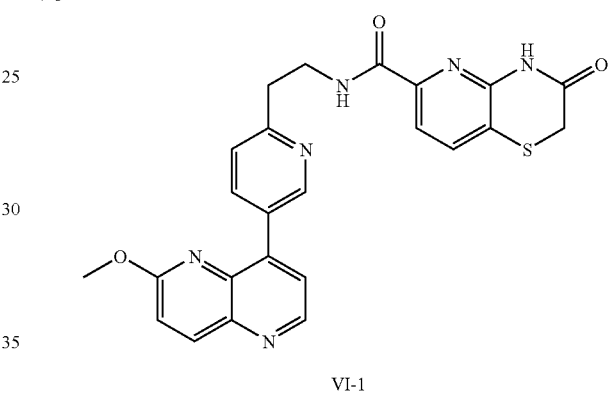

Reagents and conditions: (a) EDC, HOBt, (i-PR)₂NEt, DMF, 3-oxo-3,4-dihydro-2H-pyrido[3,2-b][1,4]thiazine-6-carboxylic acid.

A suitable carboxylic acid, for instance 3-oxo-3,4-dihydro-2H-pyrido[3,2-b][1,4]thiazine-6-carboxylic acid, is converted to an activated form using, for example, EDC and HOBt, or SOCl₂, and the activated form is subsequently reacted with an appropriate amine, for instance amine (V-3), in a suitable solvent such as DMF, CH₂Cl₂, or CH₃CN, to afford VI-1. Depending on whether acid neutralization is required, an added base, such as triethylamine (Et₃N), diisopropylethylamine ((i-Pr)₂NEt), or pyridine, may be used. Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag).

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

Biological Activity

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compounds were tested in serial two-fold dilutions ranging from 0.016 to 16 mcg/mL. Compounds were evaluated against a panel of Gram-(+) organisms, including *Staphylococcus aureus* WCUH29, *Staphylococcus epidermidis* CL7, *Streptococcus pneumoniae* 1629, *Streptococcus pyogenes* CN 10, *Enterococcus faecalis* 2, and *Enterococcus faecium* 8. In addition, compounds were evaluated against a panel of Gram-(−) strains including *E. coli* 7623 AcrABEFD+, and *Moraxella catarrhalis* Ravasio. The minimum inhibitory concentration (MIC) was determined as the lowest concentration of compound that inhibited visible growth. A mirror reader was used to assist in determining the MIC endpoint.

One skilled in the art would consider any compound with a MIC of less than 64 μg/mL to be a potential lead compound. Preferably, the compounds used in the antimicrobial assays of the present invention have a MIC value of less than 16 μg/mL.

EXPERIMENTAL AND EXAMPLES

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. E. Merck Silica Gel 60 F-254 thin layer plates were used for thin-layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of [2-(4-bromophenyl)ethyl]carbamic acid tert-butyl ester

To a stirred solution of 4-bromophenethyl amine (5.0 g, 25.0 mmole) in dry THF (50 mL) at RT was added di-tert-butyl dicarbonate (5.45 g, 25.0 mmole) in dry THF (20 mL). After 30 min, the reaction contents were concentrated under reduced pressure to give the title compound (7.50 g, 99%) as a white waxy solid: LC-MS (ES) m/e 301 $(M+H)^+$.

Preparation 2

Preparation of [2-(4-bromophenyl)methyl]carbamic acid tert-butyl ester

According to the procedure of Preparation 1, except substituting 4-bromobenzylamine hydrochloride (2.15 g, 9.66 mmole) for 4-bromophenethylamine, the title compound (2.73 g, 99%) was prepared as an off-white solid following flash chromatography on silica gel (hexanes/EtOAc, 4:1): LC-MS (ES) m/e 287 $(M+H)^+$.

Preparation 3

Preparation of 1,1,1-Trifluoromethanesulfonic acid 6-methoxy-[1,5]naphthyridin-4-yl ester a) 4-Hydroxy-6-methoxy-[1,5]-naphthyridine
5-Amino-2-methoxypyridine (55.0 g, 0.44 mole) in methanol (1000 mL) with methyl propiolate (40 mL, 0.44 mole) was stirred for 48 hours, then evaporated and the product purified by chromatography on-silica gel (dichloromethane) followed by recrystallization from dichloromethane-hexane (44.6 g, 48%). The unsaturated ester (10.5 g, 0.05 mole) in warm Dowtherm A (50 mL) was added over 3 minutes to refluxing Dowtherm A, and after a further 20 minutes at reflux the mixture was cooled and poured into diethyl ether. The precipitate was filtered to give a solid (6.26g, 70%).

b) 1,1,1-Trifluoromethanesulfonic acid 6-methoxy-[1,5]naphthyridin-4-yl ester
4-Hydroxy-6-methoxy-[1,5]naphthyridine (10 g, 0.057 mole) in dichloromethane (200 mL) containing 2,6-lutidine (9.94 mL, 0.086 mole) and 4-dimethylaminopyridine (0.07 g, 0.0057 mole) was cooled in ice and treated with trifluoromethanesulfonic anhydride (10.5 mL, 0.063 mole). After stirring for 2.5 hours the mixture was washed with saturated ammonium chloride solution, dried, evaporated and purified on silica gel (dichloromethane) to give a light yellow solid (13.2 g, 75%). LC-MS (ES) m/e 309 $(M+H)^+$.

Preparation 4

Preparation of 1,1,1-Trifluoro-methanesulfonic acid 8-fluoro-6-methoxyquinolin-4-yl ester a) 8-Fluoro-6-methoxy-quinolin-4-ol
2-Fluoro-4-methoxyphenylamine (3.80 g, 26.7 mmole) and methyl propiolate (2.37 ml, 0.267 mole) in methanol (100 ml) was stirred for 72 hours at room temperature, then heated at 50° C. for 24 hours. It was evaporated and the product purified by chromatography on silica gel (dichloromethane) to give a solid (1.66 g), a portion of which was recrystallised from dichloromethane-hexane. The unsaturated ester (0.96 g) in warm Dowtherm A (5 ml) was added over 3 minutes to refluxing Dowtherm A (15 ml), and after a further 20 minutes at reflux the mixture was cooled and poured into diethyl ether. The precipitate was filtered to give the title compound (0.50 g, 61%). MS (ES) m/e 196 $(M+H)^+$.

b) 1,1,1-Trifluoromethanesulfonic acid 8-fluoro-6-methoxy-quinolin-4-yl ester
8-Fluoro-6-methoxyquinolin-4-ol (0.48 g, 2.46 mmole) and dimethylaminopyridine (0.03 g) in dichloromethane (20 mL) and 2,6-lutidine (0.48 mL) was treated dropwise with triflic anhydride (0.48 ml) and the mixture was stirred at room temperature for 4 hours. It was washed with saturated ammonium chloride, dried, evaporated, and chromatographed on silica gel (dichloromethane) to afford a yellow solid (0.69 g, 86%). MS (ES) m/e 326 $(M+H)^+$.

Preparation 5

Preparation of 1,1,1-Trifluoromethanesulfonic acid 6,8-fluoro[1,5]naphthyridin-4-yl ester According to the procedure of Preparation 4, except substituting 2,4-difluorophenylamine (12.9 g, 100 mmole) for 2-fluoro-4-methoxyphenylamine, the title compound (2.32 g, 8%) was prepared as an off-white solid following flash chromatography on silica gel (EtOAc): LC-MS (ES) m/e 314 $(M+H)^+$.

Preparation 6

Preparation of 4-bromo-6-methoxy quinoline

To a stirred solution of 4-hydroxy-6-methoxyquinoline (1.20 g, 70.5 mmole) in DMF (60 mL) at RT was added $PBr_3$ (8.0 mL, 84.6 mmole) dropwise. After 2 h, the reaction contents were poured onto $H_2O$ (300 mL) and the product filtered and washed with $H_2O$ to give, after drying under high vacuum, the title compound (14.3 g, 87%) as a light yellow solid: LC-MS (ES) m/e 233 $(M+H)^+$.

Preparation 7

Preparation of {2-[4-(6-methoxy[1,5]naphthyridin-4-yl)phenyl]ethyl}carbamic acid tert-butyl ester To a stirred solution of 1,1,1-trifluoromethanesulfonic acid 6-methoxy[1,5]naphthyridin-4-yl ester (1.0 g, 3.24 mmole) in dry dioxane (50 mL) at RT was added bis(pinacolato)diboron (1.07 g, 4.22 mmole), potassium acetate (0.95 g, 9.72 mmole), 1,1-bis(diphenylphosphino)ferrocene (0.09 g, 0.16 mmole) and [1,1'-bis(diphenylphosphino)ferrocene]dichloropalladium(II) complexed with dichloromethane (1:1) (0.13 g, 0.16 mmole). The reaction contents were heated to 80° C.

for 24 h under nitrogen gas and then 1, 1-bis(diphenylphosphino)ferrocene (0.09 g, 0.16 mmole), [1,1'-bis(diphenylphosphino)ferrocene]dichloropalladium(II) complexed with dichloromethane (1:1) (0.13 g, 0.16 mmole), potassium carbonate (1.34 g, 9.72 mmole) and [2-(4-bromophenyl)ethyl]carbamic acid tert-butyl ester (0.97 g, 3.24 mmole) were added to the reaction pot. After 24 h of vigorous stirring at 80° C., the reaction contents were filtered through a scinter-glass funnel containing a bed of celite (EtOAc). The filtrate was concentrated under vacuum and purified on silica (EtOAc) to afford the title compound (0.76 g, 62%) as a tan solid: LC-MS (ES) m/e 380 (M+H)+.

Preparation 8

Preparation of {2-[4-(6-methoxy[1,5]naphthyridin-4-yl)phenyl]methyl}carbamic acid tert-butyl ester According to the procedure of Preparation 7, except substituting [2-(4-bromophenyl)methyl]carbamic acid tert-butyl ester (1.71 g, 6.0 mmole) for [2-(4-bromophenyl)ethyl]carbamic acid tert-butyl ester, the title compound (1.38 g, 63%) was prepared as an off-white solid following flash chromatography on silica gel (EtOAc): MS (ES) m/e 366 (M+H)+.

Preparation 9

Preparation of {2-[4-(8-fluoro-6-methoxyquinolin-4-yl)phenyl]ethyl}carbamic acid tert-butyl ester According to the procedure of Preparation 7, except substituting 1,1,1-trifluoromethanesulfonic acid 8-fluoro-6-methoxy[1,5]naphthyridin-4-yl ester (2.02 g, 4.48 mmole) for 1,1,1-trifluoromethanesulfonic acid 6-methoxy[1,5]naphthyridin-4-yl ester, the title compound (0.95 g, 53%) was prepared as an off-white solid following flash chromatography on silica gel (EtOAc): LC-MS (ES) m/e 397 (M+H)+.

Preparation 10

Preparation of {2-[4-(6,8-difluoroquinolin-4-yl)phenyl]ethyl}carbamic acid tert-butyl ester According to the procedure of Preparation 7, except substituting 1,1,1-trifluoromethanesulfonic acid 6,8-difluoro[1,5]naphthyridin-4-yl ester (2.11 g, 6.48 mmole) for 1,1,1-trifluoromethanesulfonic acid 6-methoxy[1,5]naphthyridin-4-yl ester, the title compound (1.25 g, 50%) was prepared as an off-white solid following flash chromatography on silica gel (EtOAc): LC-MS (ES) m/e 385 (M+H)+.

Preparation 11

Preparation of {2-[4-(6-methoxyquinolin-4-yl)phenyl]ethyl}carbamic acid tert-butyl ester According to the procedure of Preparation 7, except substituting 4-bromo-6-methoxyquinoline (1.26 g, 5.3 mmole) for 1,1,1-trifluoromethanesulfonic acid 6-methoxy[1,5]naphthyridin-4-yl ester, the title compound (1.33 g, 67%) was prepared as an off-white solid following flash chromatography on silica gel (EtOAc): LC-MS (ES) m/e 379 (M+H)+.

Preparation 12

Preparation of 2-methoxy-8-(5-methylpyridin-2-yl)[1,5]naphthyridine

According to the procedure of Preparation 7, except substituting 2-bromo-5-methylpyridine (1.03 g, 6.0 mmole) for [2-(4-bromophenyl)ethyl]carbamic acid tert-butyl ester, the title compound (0.72 g, 48%) was prepared as an off-white solid following flash chromatography on silica gel (EtOAc): LC-MS (ES) m/e 252 (M+H)+.

Preparation 13

Preparation of 2-methoxy-8-(6-methylpyridin-3-yl)[1.5]naphthyridine

According to the procedure of Preparation 7, except substituting 5-bromo-2-methylpyridine (1.11 g, 6.49 mmole) for [2-(4-bromophenyl)ethyl]carbamic acid tert-butyl ester, the title compound (0.81 g, 50%) was prepared as an off-white solid following flash chromatography on silica gel (EtOAc): LC-MS (ES) m/e 252 (M+H)+.

Preparation 14

Preparation of 3-Oxo-3,4-dihydro-2H-benzo[1,4]thiazine-6-carboxaldehyde a) 3-Oxo-3,4-dihydro-2H-benzo[1,4]thiazine-6-carboxylic acid 3-Oxo-3,4-dihydro-2H-benzo[1,4]thiazine-6-carboxylic acid methyl ester (6.74 g) was suspended in tetrahydrofuran (100 mL) and 2M sodium hydroxide (30 mL) was added followed by water (20 mL). The solution was stirred for 2.5 hours, evaporated to half volume and acidified with 2M hydrochloric acid. The product was collected, washed with water and dried in vacuo, to give a white solid (6.2 g).

MS (−ve ion electrospray) m/e 208 (M−H)−.

b) 6-Hydroxymethyl-4H-benzo[1,4]thiazin-3-one

3-Oxo-3,4-dihydro-2H-benzo[1,4]thiazine-6-carboxylic acid in tetrahydrofuran (50 mL) and triethylamine (4.7 mL) was cooled to 0° C. and isobutylchloroformate (4.02 mL) was added dropwise and the solution was stirred at 0° C. for 2 hours, when it was filtered into a stirred solution of sodium borohydride (3.14 g) in ice/water (50 mL). The mixture was stirred at 0° C. for 1 hour and allowed to warm to room temperature. It was acidified with 2M hydrochloric acid, evaporated to half volume, and the resulting product was collected, washed with water and dried in vacuo, to give a white solid (4.5 g).

MS (−ve ion electrospray) m/e 194 (M−H)−.

c) 3-Oxo-3,4-dihydro-2H-benzo[1,4]thiazine-6-carbaldehyde

A stirred solution of 6-hydroxymethyl-4H-benzo[1,4]thiazin-3-one (3.5 g) in chloroform (150 mL) and tetrahydrofuran (300 mL) was treated with manganese dioxide (7.8 g) for 18 hours and was filtered and evaporated to give a white solid (2.5 g).

MS (−ve ion electrospray) m/e 194 (M−H)−.

Preparation 15

Preparation of 3-Oxo-3,4-dihydro-2H-benzo[1,4]oxazine-6-carboxaldehyde a) (4-Formyl-2-nitrophenoxy)acetic acid ethyl ester A solution of 4-hydroxy-3-nitrobenzaldehyde (6.9 g) and ethyl bromoacetate (5.0 mL) in dimethylformamide (250 mL) was treated with anhydrous potassium carbonate (10 g) and the mixture was heated at 60° C. for 18 hours and evaporated to dryness. The residue was partitioned between water and diethyl ether, and the diethyl ether layer was washed with 0.5M sodium hydroxide. It was then dried over anhydrous sodium sulfate and evaporated to give an oil that was chromatographed on silica gel (ethyl acetate/dichloromethane) to afford an oil (1.9 g). MS (+ve ion electrospray) m/e 253 $(M+H)^+$.

b) 3-Oxo-3,4-dihydro-2H-benzo[1,4]oxazine-6-carboxaldehyde (4-Formyl-2-nitrophenoxy)acetic acid ethyl ester (1.9 g) in acetic acid (40 mL) was treated with iron powder (4.2 g) and the mixture was stirred at 60° C. for 0.75 hours, filtered and evaporated to dryness. It was partitioned between aqueous sodium bicarbonate and ethyl acetate. The organic fraction was chromatographed on silica gel (ethyl acetate) to give a white solid (0.88 g). MS (−ve ion electrospray) m/e 176 $(M-H)^-$.

Preparation 16

Preparation of 3-oxo-3,4-dihydro-2H-pyrido[3,2-b][1,4]thiazine-6-carboxaldehyde a) Methyl 3-oxo-3,4-dihydro-2H-pyrido[3,2-b][1,4]thiazine-6-carboxylate A solution of ethyl 2-mercaptoacetate (1.47 ml) in DMF (48 ml) was ice-cooled and treated with sodium hydride (540 mg of a 60% dispersion in oil). After 1 hour, methyl 6-amino-5-bromopyridine-2-carboxylate (3 g) (T. R. Kelly and F. Lang, *J. Org. Chem.* 61, 1996, 4623-4633) was added and the mixture stirred for 16 hours at room temperature. The solution was diluted with EtOAc (1 liter), washed with water (3×300 ml), dried and evaporated to about 10 ml. The white solid was filtered off and washed with a little EtOAc to give the ester (0.95g). MS (APCl⁻) m/e 223 ([M−H]⁻, 100%).

b) 3-Oxo-3,4-dihydro-2H-pyrido[3,2-b][1,4]thiazine-6-carboxylic acid

A solution of Methyl 3-oxo-3,4-dihydro-2H-pyrido[3,2-b][1,4]thiazine-6-carboxylate (788 mg) in dioxane (120 ml)/water (30 ml) was treated dropwise over 2 hours with 0.5M NaOH solution (8 ml) and stirred overnight. After evaporation to approx. 3 ml, water (5 ml) was added and 2N HCl to pH=4. The precipitated solid was filtered off, washed with a small volume of water and dried under vacuum to give a solid (636 mg). MS (APCl⁻) m/e 209 ([M−H]⁻, 5%),165([M−COOH]⁻, 100%).

c) 6-Hydroxymethyl-3-oxo-3,4-dihydro-2H-pyrido[3,2-b][1,4]thiazine

A solution of 3-Oxo-3,4-dihydro-2H-pyrido[3,2-b][1,4]thiazine-6-carboxylic acid (500 mg) in THF (24 mL) with triethylamine (0.4.mL) was cooled to −10° C. and isobutyl chloroformate (0.339 mL) added. After 20 minutes the suspension was filtered through celite into an ice-cooled solution of sodium borohydride (272 mg) in water (8 ml), the mixture stirred 30 minutes and the pH reduced to 7 with dilute HCl. The solvent was evaporated and the residue triturated under water. The product was filtered and dried under vacuum to give a white solid (346 mg). MS (APCl⁻) m/e 195 ([M−H]⁻, 50%), 165(100%).

d) 3-Oxo-3,4-dihydro-2H-pyrido[3,2-b][1,4]thiazine-6-carboxaldehyde

A solution of 6-Hydroxymethyl-3-oxo-3,4-dihydro-2H-pyrido[3,2-b][1,4]thiazine (330 mg) in dichloromethane (30 ml)/THF (30 ml) was treated with manganese dioxide (730 mg) and stirred at room temperature. Further manganese dioxide was added after 1 hour (730 mg) and 16 hours (300 mg). After a total of 20 hours the mixture was filtered through celite and the filtrate evaporated. The product was triturated with EtOAc/hexane (1:1) and collected to give a solid (180 mg). MS (APCl⁻) m/e 195 ([M−H]⁻, 95%), 165 (100%).

Preparation 17

Preparation of 3-Oxo-3,4-dihydro-2H-pyrido[3,2-b][1,4]oxazine-6-carboxaldehyde a) 5-Bromo-3-hydroxy-2-nitropyridine N-bromosuccinimide (165 g, 0.927 mole) was added portionwise over 5 h to a solution of 3-hydroxy-2-nitropyridine (100.0 g, 0.714 mole) in DMF (1 L) at 0° C. The resulting mixture was stirred at room temperature for 15 hr then was concentrated in vacuo. The residue was taken up in Et₂O (500 mL) and stirred for 30 min. The precipitate was removed by suction filtration, and the filtrate was concentrated in vacuo to afford the title compound (180 g): MS (ES) m/e 219 (M+H)⁺. This material was used without further purification.

b) Ethyl (6-bromo-2-nitropyridin-3-yloxy)acetate

5-Bromo-3-hydroxy-2-nitropyridine (40 g of crude material from previous reaction, 0.14 mole) was suspended in acetone (650 mL) with mechanical stirring, and K₂CO₃ (39 g, 0.28 mole) was added, followed by ethyl bromoacetate (19 mL, 0.171 mmole). The reaction was heated at reflux for 10 hr, then was cooled to room temperature and diluted with H₂O (1 L). The mixture was extracted with Et₂O (2×700 mL), and the combined organic layers were washed sequentially with H₂O and brine, dried (Na₂SO₄), and concentrated in vacuo to afford the title compound (41 g): LC-MS (ES) m/e 305 (M+H)⁺. This material was >85% pure and used without further purification.

c) 6-Bromo-4H-pyrido[3,2-b][1,4]oxazin-3-one

Ethyl (6-bromo-2-nitropyridin-3-yloxy)acetate (41 g, 0.132 mole) was dissolved in glacial AcOH (400 mL) and the solution was heated to 77° C. with mechanical stirring. Iron powder (50 g, 0.89 mole) was added portionwise over 2 hr, so that the temperature did not rise above 90° C. The mixture was mechanically stirred and heated at 77° C. for 10 hr then was cooled to room temperature and diluted with 1:4 EtOAc/CHCl₃ (1 L). The mixture was filtered through a pad of celite® and the filtrate was concentrated in vacuo. The residue was purified by flash chromatography on silica gel (1 kg; 0-10% EtOAc/CHCl₃) to afford the title compound (21.5 g, 70%): MS (ES) m/e 229 (M+H)⁺.

d) 6-((E)-Styryl)-4H-pyrido[3,2-b][1,4]oxazin-3-one

6-Bromo-4H-pyrido[3,2-b][1,4]oxazin-3-one (10.0 g, 44 mmole) and trans-2-phenylvinylboronic acid (9.0 g, 61 mmole), were dissolved in 1,4-dioxane (200 mL) and the solution was degassed with argon. (Ph₃P)₄Pd (2.5 g, 2.2 mmole) was added, followed by a solution of K₂CO₃ (15 g, 109 mmole) in H$_2$O (100 mL). The reaction was heated at reflux under argon overnight, then was cooled to room temperature and diluted with chloroform (400 mL). The solution was washed sequentially with H$_2$O and brine, dried (Na$_2$SO$_4$), and concentrated in vacuo. The solid residue was recrystallized from hot EtOAc to afford the title compound (6.4 g, 57.5%): LC-MS (ES) m/e 253 (M+H)$^+$.

e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (6.2 g, 27 mmole) was dissolved in 5:1 CH$_2$Cl$_2$/MeOH (500 mL) and the solution was cooled to −78° C. Ozone was bubbled through the solution with stirring until a pale blue color appeared, then the excess ozone was removed by bubbling oxygen through the solution for 15 min. Dimethylsulfide (9.9 mL, 135 mmole) was added to the solution, and the reaction was stirred at −78° C. for 3 hr, then at room temperature overnight. The solvent was removed in vacuo, and the residue was triturated and stirred with Et$_2$O (150 mL). The solid was collected by suction filtration, washed with additional Et$_2$O, and dried to afford the title compound (3.4 g, 77%): LC-MS (ES) m/e 179 (M+H)$^+$.

Preparation 18

Preparation of
3-oxo-3,4-dihydro-2H-benzo[1,4]thiazine-6-sulfonyl chloride

Powdered 4H-benzo[1,4]thiazin-3-one (7.0 g) was added cautiously, portionwise (over 20 minutes), to chlorosulfonic acid (15 mL), cooled in ice. After 1 hour, the blue solution was allowed to warm to room temperature and it was heated at 45° C. for 2 hours, cooled and poured into ice. The solid was collected, washed with water, and hexane, and dried in vacuo, to give a white solid (7.0 g): LC-MS (ES) m/e 263 (M)$^+$.

Preparation 19

Preparation of 2-Oxo-2,3-dihydro-1H-pyrido[2,3-b][1,4]thiazine-7-carboxaldehyde a) 6-Methoxycarbonylmethylsulfanyl-5-nitro-nicotinic acid methyl ester A solution of 6-chloro-5-nitronicotinic acid methyl ester (1.0 g) [prepared as described by A. H. Berrie et al. *J. Chem. Soc.* 2590-2594 (1951)] in dichloromethane (10 mL) containing triethylamine (0.76 mL) was treated with mercapto-acetic acid methyl ester (0.44 mL) and the solution was stirred at room temperature for 1 hour and evaporated to dryness. Sodium bicarbonate solution was added and the mixture was extracted with dichloromethane, dried (anhydrous sodium sulfate) and evaporated to afford a solid (1.0 g). MS (ES) m/e 287 (M+H)$^+$.

b) 2-Oxo-2,3-dihydro-1H-pyrido[2,3-b][1,4]thiazine-7-carboxylic acid methyl ester 6-Methoxycarbonylmethylsulfanyl-5-nitro-nicotinic acid methyl ester (1.0 g) in acetic acid (50 mL) was treated with iron powder (10 g) and the mixture was stirred and heated at 60° C. for 1 hour, cooled and filtered. The filtrate was evaporated, treated with sodium bicarbonate solution and extracted with warm chloroform. It was dried (anhydrous sodium sulfate) and evaporated to give a white solid (0.85 g).

MS (ES) m/e 225 (M+H)$^+$.

c) 2-Oxo-2,3-dihydro-1H-pyrido[2,3-b][1,4]thiazine-7-carboxylic acid

2-Oxo-2,3-dihydro-1H-pyrido[2,3-b][1,4]thiazine-7-carboxylic acid methyl ester (2.8 g) was hydrolyzed with aqueous sodium hydroxide in tetrahydrofuran by the method of Preparation (14a) to afford a solid (2.5 g). MS (−ve ion electrospray) m/e 209 (M−H$^-$).

d) 7-Hydroxymethyl-1H-pyrido[2,3-b][1,4]thiazin-2-one

2-Oxo-2,3-dihydro-1H-pyrido[2,3-b][1,4]thiazine-7-carboxylic acid (2.48 g) was reacted with iso-butylchloroformate and sodium borohydride by the method of Preparation (14b) to afford a solid (1.3 g), after recrystallisation from chloroform-methanol (9:1). MS (ES) m/e 197 (M+H)$^+$.

e) 2-Oxo-2,3-dihydro-1H-pyrido[2,3-b][1,4]thiazine-7-carboxaldehyde

7-Hydroxymethyl-1H-pyrido[2,3-b][1,4]thiazin-2-one (1.22 g) was oxidized with manganese dioxide by the method of Preparation (14c) to afford a solid (0.7 g).

MS (−ve ion electrospray) m/e 193 (M−H$^-$).

Preparation 20

Preparation of 7-fluoro-2,3-dihydrobenzo[1,4]dioxine-6-carboxaldehyde

7-Fluoro-2,3-dihydrobenzo[1,4]dioxine-6-carboxaldehyde was prepared from 6-fluoro-2,3-dihydrobenzo[1,4]dioxine [V. Daukas et al Chemija, 1999, 10 (1), 59] by reaction of dichloromethyl methyl ether and titanium tetrachloride: LC-MS (ES) m/e 155 (M+H)$^+$.

Preparation 21

Preparation of
6-(2-Chloroethyl)-4H-benzo[1,4]oxazin-3-one

To a dried flask under N$_2$ atmosphere equipped with addition funnel was added 6-(2-chloroethanoyl)-4H-benzo[1,4]oxazin-3-one (10.0 g, 44.4 mmol) in trifluoroacetic acid (34 mL, 0.44 mol). To the resulting mixture at 0° C. was added triethylsilane (15.3 mL, 0.1 mole) dropwise over 5 min. The resulting mixture was warmed to 45° C. for 30 min and stirred at room temperature for 40 h. Reaction was poured onto ice water and layered with EtOAc. The organic layer was washed with water, brine, and dried over MgSO$_4$. Solvent was removed on vacuum to give the desired compound as white solid (9.0 g, 93%). LC-MS (ES): m/e 212 (M+H)$^+$.

Preparation 22

Preparation of toluene-4-sulfonic acid 2-(3-oxo-3,4-dihydro-2H-benzo[1,4]thaizin-6-yl)ethyl ester a) 6-Vinyl-4H-benzo[1,4]thiazin-3-one To a stirred suspension of triphenylmethylphosphonium bromide (20.0 mmole) in dry THF (40 mL) at RT was added 2.5 M n-BuLi (7.5 mL, 3.0 mmole). After 3 h, 3-oxo-3,4-dihydro-2H-benzo[1,4]thiazine-6-carboxaldehyde (1.93 g, 10.0 mmole) was added and the reaction contents were stirred at RT overnight. The reaction solution was filtered and the filtrate concentrated, dissolved in EtOAc and washed with 1 M HCl (20 mL). The organic solution was dried (Na$_2$SO$_4$) and concentrated under vacuum. Purification on silica (EtOAc/hexanes, 1:4) afforded the title compound (1.20 g, 63%) as light yellow solid: LC-MS (ES): m/e 192 (M+H)$^+$.

b) 6-(2-Hydroxyethyl) 4H-benzo[1,4]thiazin-3-one

To a stirred solution of 6-vinyl-4H-benzo[1,4]thiazin-3-one (5.73 g, 30.0 mmole) in dry THF (100 mL) at RT was added 2M BH$_3$.THF (7.5 mL, 15.0 mmole). After 24 h, H$_2$O (15 mL) was slowly added to the reaction mixture followed by 3M NaOH (5 mL) and 30% H$_2$O$_2$ (3.3 mL). After the reaction solution was stirred for 3 h at 50° C., the reaction was concentrated under vacuum. The residue was dissolved in EtOAc and washed with H$_2$O (20 mL) and 1M HCl (20 mL). The organic solution was dried (Na$_2$SO$_4$), concentrated under vacuum, and the remaining solid purified on silica (CH$_2$Cl$_2$/CH$_3$OH, 95:5) afforded the title compound (2.60 g, 41%) as light yellow solid: LC-MS (ES): m/e 210 (M+H)$^+$.

c) Toluene-4-sulfonic acid 2-(3-oxo-3,4-dihydro-2H-benzo[1,4]thaizin-6-yl)ethyl ester To a stirred solution of 6-(2-hydroxyethyl) 4H-benzo[1,4]thiazin-3-one (2.09 g, 10.0 mmole) in dry pyridine (25 mL) at RT was added p-toluenesulfonyl chloride (10.0 mmole). After 24 h, the reaction solution was concentrated under vacuum. Purification on silica (EtOAc/hexanes, 1:1) afforded the title compound (0.91 g, 47%) as light yellow solid: LC-MS (ES): m/e 192 (M+H)$^+$.

Preparation 23

Preparation of 1,1-dimethylethyl [2-(5-bromo-2-pyridinyl)ethyl]carbamate a) 5-bromo-2-(bromomethyl)pyridine To a stirred solution of 5-bromo-2-methylpyridine (1.2 g, 4.78 mmole), in dry CCl$_4$ (150 mL) at RT was added NBS (1.02 g, 5.73 mmole) and benzoylperoxide (0.12 g, 0.48 mmole). After 18 h at reflux, the reaction contents were cooled to RT and filtered through a scintered-glass funnel washing with CHCl$_3$. Concentration under vacuum and purification on silica (EtOAc) afforded the title compound (1.12 g, 71%) as light yellow solid: (EtOAc): LC-MS (ES) m/e 330 (M)$^+$.

b) (5-bromo-2-pyridinyl)acetonitrile

To a stirred solution of 5-bromo-2-(bromomethyl)pyridine (0.70 g, 2.12 mmole), in EtOH (50 mL) at 60° C. was added KCN (0.21 g, 3.18 mmole) in H$_2$O (3 mL). After 1.5 h, the reaction contents were cooled to RT and concentrated under vacuum. The aqueous residue was dissolved in EtOAc and washed with H$_2$0, and dried over Na$_2$SO$_4$. Concentration under vacuum and purification on silica (EtOAc) afforded the title compound (0.38 g, 65%) as light yellow solid: LC-MS (ES) m/e 277 (M+H)$^+$.

c) [2-(5-bromo-2-pyridinyl)ethyl]amine

To a stirred solution of (5-bromo-2-pyridinyl)acetonitrile (0.26 g, 0.94 mmole), in THF (20 mL) at RT was added 1M BH$_3$.THF (5 mL, 5.0 mmole). After 24 h, H$_2$O (10 mL) wash added dropwise to the reaction solution followed by 1M HCl (10 mL). After 1 h, the reaction solution was made basic by addition of 6M NaOH (2 mL). The reaction contents were concentrated under vacuum and extracted with EtOAc (3×50 mL). The organic phase was dried over Na$_2$SO$_4$ and concentrated under vacuum affording the crude title compound as light orange solid which was used directly without further purification: LC-MS (ES) m/e 281 (M+H)$^+$.

(d) 1,1-dimethylethyl [2-(5-bromo-2-pyridinyl)ethyl]carbamate

To a stirred solution of [2-(5-bromo-2-pyridinyl)ethyl]amine (5.0 g, 25.0 mmole) in dry THF (50 mL) at RT was added di-tert-butyl dicarbonate (5.45 g, 25.0 mmole) in dry THF (20 mL). After 30 min, the reaction contents were concentrated under reduced pressure to give the title compound (7.50 g, 99%) as a white waxy solid: LC-MS (ES) m/e 301 (M+H)$^+$.

Preparation 24

Preparation of 1,1-dimethylethyl [2-(6-chloro-3-pyridinyl)ethyl]carbamate

According to the procedure of Preparation 1, except substituting 2-chloro-5-methylpyridine (1.71 g, 6.0 mmole) for 5-bromo-2-methylpyridine, the title compound (1.38 g, 63%) was prepared as an off-white solid following flash chromatography on silica gel (EtOAc): MS (ES) m/e 366 (M+H)$^+$.

Example 1

Preparation of 6-({2-[4-(6-Methoxy-[1,5]naphthyridin-4-yl)phenyl]ethylamino}methyl)-4H-benzo[1,4]thiazin-3-one a) 2-[4-(6-Methoxy-[1,5]naphthyridin-4-yl)phenyl]ethylamine hydrochloride salt To a stirred solution of {2-[4-(6-methoxy[1,5]naphthyridin-4-yl)phenyl]ethyl}carbamic acid tert-butyl ester (0.67 g, 1.76 mmole) in dry CH$_2$Cl$_2$ (75 mL) at RT was added trifluoroacetic acid (50 mL). After 2 h, the reaction solution was concentrated under vacuum and the residue dissolved in 4M HCl in dioxane (5 mL) at RT. After 1 hr, the reaction contents were concentrated and dried under high vacuum to give the crude title compound as a tan solid which was used immediately in the proceeding reaction: LC-MS (ES) m/e 280 (M+H)$^+$.

b) 6-({2-[4-(6-Methoxy-[1,5]naphthyridin-4-yl)phenyl]ethylamino}methyl)-4H-benzo[1,4]thiazin-3-one To a stirred solution of 2-[4-(6-Methoxy-[1,5]naphthyridin-4-yl)phenyl]ethylamine hydrochloride salt (1.76 mmole) in dry CH$_2$Cl$_2$ (25 mL) and dry EtOH (10 mL) at RT was added triethylamine (0.74 mL, 5.28 mmole) and 3-oxo-3,4-dihydro-2H-benzo[1,4]thiazine-6-carboxaldehyde (0.34 g, 1.76 mmole). After 24 h, the reaction contents were concentrated and dried under high vacuum. To a stirred solution of the crude imine in dry EtOH (25 mL) at RT was added NaBH$_4$ (0.66 g, 1.76 mmole). After 24 h, the reaction solution was concentrated under vacuum and to the residue was added 1M HCl (5 mL) and EtOAc (50 mL): After stirring for 1 h, 6M NaOH (1 mL) was added and the organic layer was separated, dried (Na$_2$SO$_4$) and concentrated. Purification on silica (CHCl$_3$/MeOH, 9:1 containing 5% NH$_4$OH) afforded the title compound (0.55 g, 69%) as light yellow solid: $^1$H NMR (400 MHz, CD$_3$OD) δ 9.11 (d, J=4.5 Hz, 1H), 8.57 (d, J=9.1 Hz, 1H), 8.27 (d, J=4.5 Hz, 1H), 8.14 (m, 2H), 7.90 (s, 2H), 7.61 (m, 3H), 7.46 (d, J=7.1 Hz, 1H), 7.22 (m, 2H), 5.52 (m, 2H), 4.23 (s, 2H), 4.08 (s, 3H), 3.68 (s, 2H), 3.19 (m, 2H). LC-MS (ES) m/e 457 (M+H)$^+$.

Example 2

Preparation of 6-({2-[4-(6-Methoxy-[1,5]naphthyridin-4-yl)phenyl]ethylamino}methyl)-4H-pyrido[3,2-b][1,4]thiazin-3-one According to the procedure of Example 1, except substituting 3-oxo-3,4-dihydro-2H-pyrido[2,3-b][1,4]thiazine-6- carboxaldehyde (0.15 g, 0.76 mmole) for 3-oxo-3,4-dihydro-2H-benzo[1,4]thiazine-6-carboxaldehyde, the title compound (0.21 g, 61%) was prepared as an off-white solid following flash chromatography on silica gel (CHCl$_3$/MeOH, 9:1, containing 5% NH$_4$OH): $^1$H NMR (400 MHz, CDCl$_3$) δ 8.72 (d, J=4.5 Hz, 1H), 8.20 (d, J=9.0 Hz, 1H), 7.71 (d, J=8.1 Hz, 2H), 7.47 (m, 2H), 7.23 (m, 2H), 7.03 (d, J=9.0 Hz, 1H), 6.86 (d, J=7.9 Hz, 1H), 3.86 (s, 3H), 3.80 (s, 2H), 3.35 (s, 2H), 2.86 (m, 4H). LC-MS (ES) m/e 458 (M+H)$^+$.

Example 3

Preparation of 6-({2-[4-(6-Methoxyquinolin-4-yl)phenyl]ethylamino}methyl)-4H-pyrido[3,2-b][1,4]oxazin-3-one According to the procedure of Example 1, except substituting {2-[4-(6-methoxyquinolin-4-yl)phenyl]ethyl}carbamic acid tert-butyl ester (0.31 g, 0.82 mmole) for {2-[4-(6-methoxy[1,5]naphthyridin-4-yl)phenyl]ethyl}carbamic acid tert-butyl ester, and substituting 2-oxo-2,3-dihydro-1H-pyrido[2,3-b][1,4]thiazine-7-carboxaldehyde (0.18 g, 0.9 mmole) for 3-oxo-3,4-dihydro-2H-benzo[1,4]thiazine-6-carboxaldehyde, the title compound (0.14 g, 37%) was prepared as an off-white solid following flash chromatography on silica gel (CHCl$_3$/MeOH, 9:1, containing 5% NH$_4$OH): $^1$H NMR (400 MHz, d$_6$-DMSO) δ 10.89 (br s, 1H), 8.77 (d, J=4.5 Hz, 1H), 8.02 (d, J=9.1 Hz, 1H), 7.73 (d, J=7.8 Hz, 1H), 7.52 (d, J=8.0 Hz, 1H), 7.46 (m, 1H), 7.38 (d, J=4.4 Hz, 1H), 7.22 (d, J=2.8 Hz, 1H), 7.07 (d, J=7.9 Hz, 1H), 3.76 (s, 3H), 3.53 (s, 2H), 3.38 (m, 2H), 3.20 (m, 2H), 2.86 (m, 2H). LC-MS (ES) m/e 457 (M+H)$^+$.

Example 4

Preparation of 7-({2-[4-(6-Methoxy-[1,5]naphthyridin-4-yl)phenyl]ethylamino}methyl)-1H-pyrido[3,2-b][1,4]thiazin-2-one According to the procedure of Example 1, except substituting 3-oxo-3,4-dihydro-2H-pyrido[3,2-b][1,4]thiazine-6-carboxaldehyde (0.14 g, 0.70 mmole) for 3-oxo-3,4-dihydro-2H-benzo[1,4]thiazine-6-carboxaldehyde, the title compound (0.17 g, 58%) was prepared as an off-white solid following flash chromatography on silica gel (CHCl$_3$/MeOH, 9:1, containing 5% NH$_4$OH): $^1$H NMR (400 MHz, d$_6$-DMSO) δ 10.63 (br s, 1H), 8.83 (d, J=4.5 Hz, 1H), 8.32 (d, J=9.1 Hz, 1H), 8.05 (s, 1H), 7.87 (d, J=7.8 Hz, 2H), 7.72 (d, J=4.6 Hz, 1H), 7.38 (m, 2H), 7.26 (m, 2H), 3.92 (s, 3H), 3.71 (s, 2H), 3.63 (s, 2H), 2.81 (m, 4H). LC-MS (ES) m/e 458 (M+H)$^+$.

Example 5

Preparation of 6-({2-[4-(6-Methoxy-[1,5]naphthyridin-4-yl)phenyl]ethylamino}methyl)-4H-pyrido[3,2-b][1,4]oxazin-3-one According to the procedure of Example 1, except substituting 3-oxo-3,4-dihydro-2H-pyrido[3,2-b][1,4]oxazine-6-carboxaldehyde (0.13 g, 0.76 mmole) for 3-oxo-3,4-dihydro-2H-benzo[1,4]thiazine-6-carboxaldehyde, the title compound (0.20 g, 60%) was prepared as an off-white solid following flash chromatography on silica gel (CHCl$_3$/MeOH, 9:1, containing 5% NH$_4$OH): $^1$H NMR (400 MHz, CDCl$_3$) δ 8.74 (d, J=4.5 Hz, 1H), 8.21 (d, J=9.0 Hz, 1H), 7.70 (d, J=8.1 Hz, 2H), 7.44 (d, J=4.6 Hz, 1H), 7.25 (m, 2H), 7.08 (m, 2H), 6.83 (d, J=8.1 Hz, 1H), 4.52 (s, 2H), 3.86 (s, 3H), 3.80 (s, 2H), 2.86 (m, 4H). LC-MS (ES) m/e 442 (M+H)$^+$.

Example 6

Preparation of 3-Oxo-3,4-dihydro-2H-benzo[1,4]thiazine-6-sulfonic acid {2-[4-(6-methoxy-[1,5]naphthyridin-4-yl)phenyl]ethyl}amide To a stirred solution of 2-[4-(6-Methoxy-[1,5]naphthyridin-4-yl)phenyl]ethylamine hydrochloride salt (0.10 g, 0.26 mmole), from Example 1a, in dry CH$_2$Cl$_2$ (25 mL) at RT was added triethylamine (0.11 mL, 0.78 mmole) and 3-oxo-3,4-dihydro-2H-benzo[1,4]thiazine-6-sulfonyl chloride (69 mg, 0.26 mmole). After 24 h, the reaction contents were concentrated. Purification on silica (CHCl$_3$/MeOH, 9:1 containing 5% NH$_4$OH) afforded the title compound (0.10 g, 75%) as light yellow solid: $^1$H NMR (400 MHz, CD$_3$OD) δ 9.06 (d, J=4.5 Hz, 1H), 8.57 (d, J=9.0 Hz, 1H), 8.26 (d, J=4.6 Hz, 1H), 8.10 (d, J=9.1 Hz, 2H), 7.73 (m, 3H), 7.45 (d, J=9.0, 1H), 7.17 (m, 2H), 4.25 (s, 2H), 4.06 (s, 3H), 3.77 (m, 2H), 3.31 (m, 2H). LC-MS (ES) m/e 507 (M+H)$^+$.

Example 7

Preparation of {2-[4-(6-Methoxy-[1,5]naphthyridin-4-yl)phenyl]ethyl}(5,6,7,8-tetrahydro[1,8]naphthyridin-2-ylmethyl)amine According to the procedure of Example 1, except substituting 5,6,7,8-tetrahydro[1,8]naphthyridine-2-carboxaldehyde [Merck Patent WO 98/08840] (0.16 g, 1.0 mmole) for 3-oxo-3,4-dihydro-2H-benzo[1,4]thiazine-6-carboxaldehyde, the title compound (0.26 g, 62%) was prepared as an off-white solid following flash chromatography on silica gel (CHCl$_3$/MeOH, 9:1, containing 5% NH$_4$OH): $^1$H NMR (400 MHz, CDCl$_3$) δ 8.81 (d, J=4.5 Hz, 1H), 8.25 (d, J=9.0 Hz, 1H), 7.83 (d, J=8.2 Hz, 2H), 7.59 (d, J=4.5 Hz, 1H), 7.36 (d, J=8.1 Hz, 1H), 7.15 (d, J=9.0 Hz, 1H), 7.09 (d, J=7.3 Hz, 1H), 6.47 (d, J=7.3 Hz, 1H), 4.79 (br s, 1H), 4.00 (s, 3H), 3.73 (s, 2H), 3.36 (m, 2H), 2.97 (m, 4H), 2.71 (m, 2H), 1.91 (m, 2H). LC-MS (ES) m/e 426 (M+H)$^+$.

Example 8

Preparation of 6-{2-[4-(6-Methoxy-[1,5]naphthyridin-4-yl)benzylamino]ethyl}-4H-benzo[1,4]oxazin-3-one a) 2-[4-(6-methoxy-[1,5]naphthyridin-4-yl)phenyl]methylamine trihydrochloride salt According to the procedure of Example 1a, except substituting {2-[4-(6-methoxy[1,5]naphthyridin-4-yl)phenyl]methyl}carbamic acid tert-butyl ester (2.33 g, 6.38 mmole) for {2-[4-(6-methoxy[1,5]naphthyridin-4-yl)phenyl]methyl}carbamic acid tert-butyl ester, the crude title compound (2.35 g, 99%) was prepared as an off-white solid: LC-MS (ES) m/e 266 (M+H)$^+$.

b) 6-{2-[4-(6-Methoxy-[1,5]naphthyridin-4-yl)benzylamino]ethyl}-4H-benzo[1,4]oxazin-3-one To a stirred solution of 2-[4-(6-methoxy-[1,5]naphthyridin-4-yl)phenyl]methylamine trihydrochloride salt (0.42 g, 1.14 mmole), from Example 8a, in dry acetonitrile (50 mL) at RT was added K$_2$CO$_3$ (0.79 g, 5.70 mmole), KI (cat.) and 6-(2-chloroethyl)-4H-benzo[1,4]oxazin-3-one (0.24 g, 1.14 mmole). After 72 h at reflux, the reaction contents were cooled to RT and concentrated. Purification on silica (CHCl₃/MeOH, 9:1 containing 5% NH₄OH) afforded the title compound (0.20 g, 40%) as light yellow solid: (CHCl₃/MeOH, 9:1, containing 5% NH₄OH): $^1$H NMR (400 MHz, CDCl₃) δ 8.81 (d, J=4.5 Hz, 1H), 8.28 (d, J=9.0 Hz, 1H), 7.85 (d, J=8.1 Hz, 2H), 7.57 (d, J=4.6 Hz, 1H), 7.44 (m, 2H), 7.14 (d, J=9.0, 1H), 6.83 (m, 2H), 6.63 (s, 1H), 4.59 (s, 2H), 3.96 (s, 3H), 3.92 (s, 2H), 2.97 (m, 2H), 2.79 (m, 2H). LC-MS (ES) m/e 441 (M+H)⁺.

Example 9

Preparation of 6-{2-[4-(6-Methoxy-[1,5]naphthyridin-4-yl)benzylamino]ethyl}-4H-benzo[1,4]thiazin-3-one According to the procedure of Example 8, except substituting toluene-4-sulfonic acid 2-(3-oxo-3,4dihydro-2H-benzo[1,4]thiazin-6-yl)ethyl ester (0.16 g, 0.44 mmole) for 6-(2-chloroethyl)-4H-benzo[1,4]oxazin-3-one, the crude title compound (84 mg, 42%) was prepared as an off-white solid: $^1$H NMR (400 MHz, CDCl₃) δ 9.16 (br s, 1H), 8.84 (d, J=4.5 Hz, 1H), 8.27 (d, J=9.0 Hz, 1H), 7.86 (d, J=8.1 Hz, 2H), 7.58 (d, J=4.6 Hz, 1H), 7.44 (d, J=8.2 Hz, 2H), 7.23 (d, J=7.9 Hz, 1H), 7.16 (d, J=9.0, 1H), 6.93 (m, 1H), 6.76 (s, 1H), 3.96 (s, 3H), 3.92 (s, 2H), 3.42 (s, 2H), 2.97 (m, 2H), 2.83 (m, 2H). LC-MS (ES) m/e 457 (M+H)⁺.

Example 10

Preparation of 6-({2-[6-(6-methoxy-[1,5]naphthyridin-4-yl)pyridin-3-yl]ethylamino}methyl)-4H-pyrido[3,2-b][1,4]thiazin-3-one a) 8-(5-bromomethylpyridin-2-yl)-2-methoxy[1,5]naphthyridine To a stirred solution of 2-methoxy-8-(5-methylpyridin-2-yl)[1,5]naphthyridine (1.2 g, 4.78 mmole), in dry CCl₄ (150 mL) at RT was added NBS (1.02 g, 5.73 mmole) and benzoylperoxide (0.12 g, 0.48 mmole). After 18 h at reflux, the reaction contents were cooled to RT and filtered through a scintered-glass funnel washing with CHCl₃. Concentration under vacuum and purification on silica (EtOAc) afforded the title compound (1.12 g, 71%) as light yellow solid: (EtOAc): LC-MS (ES) m/e 330 (M)⁺.

b) [6-(6-methoxy[1,5]naphthyridin-4-yl)pyridin-3-yl]acetonitrile

To a stirred solution of 8-(5-bromomethylpyridin-2-yl)-2-methoxy[1,5]naphthyridine (0.70 g, 2.12 mmole), in EtOH (50 mL) at 60° C. was added KCN (0.21 g, 3.18 mmole) in H₂O (3 mL). After 1.5 h, the reaction contents were cooled to RT and concentrated under vacuum. The aqueous residue was dissolved in EtOAc and washed with H₂O, and dried over Na₂SO₄. Concentration under vacuum and purification on silica (EtOAc) afforded the title compound (0.38 g, 65%) as light yellow solid: LC-MS (ES) m/e 277 (M+H)⁺.

c) 2-[6-(6-methoxy[1,5]naphthyridin-4-yl)pyridin-3-yl]ethylamine

To a stirred solution of [6-(6-methoxy[1,5]naphthyridin-4-yl)pyridin-3-yl]acetonitrile (0.26 g, 0.94 mmole), in THF (20 mL) at RT was added 1M BH₃.THF (5 mL, 5.0 mmole). After 24 h, H₂O (10 mL) wash added dropwise to the reaction solution followed by 1M HCl (10 mL). After 1 h, the reaction solution was made basic by addition of 6M NaOH (2 mL). The reaction contents were concentrated under vacuum and extracted with EtOAc (3×50 mL). The organic phase was dried over Na₂SO₄ and concentrated under vacuum affording the crude title compound as light orange solid which was used directly without further purification: LC-MS (ES) m/e 281 (M+H)⁺.

d) 6-({2-[6-(6-methoxy-[1,5]naphthyridin -4-yl)pyridin-3-yl]ethylamino}methyl)-4H-pyrido[3,2-b][1,4]thiazin-3-one To a stirred solution of 2-[6-(6-methoxy[1,5]naphthyridin-4-yl)pyridin-3-yl]ethylamine (0.94 mmole) in dry CH₂Cl₂ (25 mL) and dry EtOH (10 mL) at RT was added 3-oxo-3,4-dihydro-2H-pyrido[3,2-b][1,4]thiazine-6-carboxaldehyde (0.18 g, 0.94 mmole) and Na₂SO₄ (500 mg). After 24 h, the reaction contents were concentrated and dried under high vacuum. To a stirred solution of the crude imine in dry EtOH (25 mL) at RT was added NaBH₄ (36 mg, 0.94 mmole). After 24 h, the reaction solution was concentrated under vacuum and to the residue was added 1M HCl (5 mL) and EtOAc (50 mL). After stirring for 1 h, 6M NaOH (1 mL) was added and the organic layer was separated, dried (Na₂SO₄) and concentrated. Purification on reverse-phase HPLC (CH₃CN/H₂O, 10-90%) afforded the title compound (0.13 g, 30%) as light yellow solid: $^1$H NMR (400 MHz, CDCl₃) δ 9.89 (br s, 1H), 9.15 (m, 1H), 8.90 (m, 1H), 8.57 (d, J=9.1 Hz, 1H), 8.45 (d, J=9.1 Hz, 1H), 8.20 (m, 2H), 7.51 (m, 1H), 7.22 (d, J=9.1 Hz, 1H), 6.88 (d, J=7.9 Hz, 1H), 4.24 (m, 2H), 4.02 (s, 3H), 3.55 (m, 2H), 3.41 (m, 2H), 3.30 (s, 2H). LC-MS (ES) m/e 459 (M+H)⁺.

Example 11

Preparation of 6-({2-[6-(6-methoxy-[1,5]naphthyridin-4-yl)pyridin-3-yl]ethylamino}methyl)-4H-pyrido[3,2-b][1,4]oxazin-3-one According to the procedures of Example 10, except substituting 3-oxo-3,4-dihydro-2H-pyrido[3,2-b][1,4]oxazine-6-carboxaldehyde (0.14 g, 0.78 mmole), for 3-oxo-3,4-dihydro-2H-pyrido[3,2-b][1,4]thiazine-6-carboxaldehyde, the title compound (45 mg) was prepared as a light yellow solid: $^1$H NMR (400 MHz, CH₃OH-d₄) δ 9.12 (m, 2H), 8.75 (m, 1H), 8.53 (m, 3H), 7.57 (d, J=9.1 Hz, 1H), 7.37 (m, 1H), 7.14 (d, J=7.6 Hz, 1H), 4.70 (m, 2H), 4.36 (s, 2H), 4.12 (s, 3H), 3.46 (m, 2H), 3.30 (m, 2H). LC-MS (ES) m/e 443 (M+H)⁺.

Example 12

Preparation of 6-({2-[5-(6-methoxy-[1,5]naphthyridin-4-yl)pyridin-2-yl]ethylamino}methyl)-4H-pyrido[3,2-b][1,4]thiazin-3-one According to the procedures of Example 10, except substituting 2-methoxy-8-(6-methylpyridin-2-yl)[1,5]naphthyridine (0.42 g, 1.67 mmole), for 2-methoxy-8-(5-methylpyridin-3-yl)[1,5]naphthyridine, the title compound (45 mg, 6% for 4 steps) was prepared as a light yellow solid: $^1$H NMR (400 MHz, CDCl₃) δ 9.49 (br s, 1H), 9.19 (m, 1H), 8.83 (d, J=4.9 Hz, 1H), 8.47 (d, J=9.1 Hz, 1H), 8.40 (d, J=9.1 Hz, 1H), 7.69 (m, 2H), 7.52 (d, J=7.8 Hz, 1H), 7.22 (d, J=9.1 Hz, 1H), 6.91 (d, J=7.9 Hz, 1H), 4.80 (m, 2H), 3.92 (s, 3H), 3.68 (m, 2H), 3.55 (m, 2H), 3.30 (s, 2H), LC-MS (ES) m/e 459 (M+H)⁺.

Example 13

Preparation of 6-({2-[4-(6,8-difluoroquinolin-4-yl) phenyl]ethylamino}methyl)-4H-pyrido[3,2-b][1,4]thiazin-3-one According to the procedure of Example 1, except substituting {2-[4-(6,8-difluoroquinolin-4-yl)phenyl]ethyl}carbamic acid tert-butyl ester (0.13 g, 0.35 mmole) for {2-[4-(6-methoxy[1,5]naphthyridin-4-yl)phenyl]ethyl}carbamic acid tert-butyl ester, and substituting 2-oxo-2,3-dihydro-1H-pyrido[2,3-b][1,4]thiazine-7-carboxaldehyde (68 mg, 0.35 mmole) for 3-oxo-3,4-dihydro-2H-benzo[1,4]thiazine-6-carboxaldehyde, the title compound (34 mg, 21%) was prepared as an off-white solid following flash chromatography on silica gel (CHCl$_3$/MeOH, 9:1, containing 5% NH$_4$OH): $^1$H NMR (400 MHz, CD$_3$OD) δ 9.22 (d, J=4.5 Hz, 1H), 7.35-8.26 (m, 9H), 4.44 (s, 3H), 3.60 (s, 2H), 3.45 (m, 2H), 3.32 (s, 2H), 3.28 (m, 2H). LC-(MS) (ES) m/e 463 (M+H)$^+$.

Example 14

Preparation of 6-({2-[4-(8-Fluoro-6-methoxyquinolin-4-yl)phenyl]ethylamino}methyl)-4H-pyrido[3,2-b][1,4]thiazin-3-one According to the procedure of Example 1, except substituting {2-[4-(8-fluoro-6-methoxyquinolin-4-yl)phenyl]ethyl}carbamic acid tert-butyl ester (0.13 g, 0.35 mmole) for {2-[4-(6-methoxy[1,5]naphthyridin-4-yl)phenyl]ethyl}carbamic acid tert-butyl ester, and substituting 2-oxo-2,3-dihydro-1H-pyrido[2,3-b][1,4]thiazine-7-carboxaldehyde (68 mg, 0.35 mmole) for 3-oxo-3,4-dihydro-2H-benzo[1,4]thiazine-6-carboxaldehyde, the title compound (38 mg, 23%) was prepared as an off-white solid following flash chromatography on silica gel (CHCl$_3$/MeOH, 9:1, containing 5% NH$_4$OH): $^1$H NMR (400 MHz, CD$_3$OD) δ 9.22 (d, J=4.5 Hz, 1H), 8.21 (d, J=9.0 Hz, 1H), 8.06 (m, 1H), 7.70-7.85 (m, 6H), 7.13 (d, J=9.0 Hz, 1H), 4.44 (s, 3H), 3.60 (s, 2H), 3.45 (m, 2H), 3.32 (s, 2H), 3.28 (m, 2H). LC-MS (ES) m/e 475 (M+H)$^+$.

Example 15

Preparation of (7-Fluoro-2,3-dihydrobenzo[1,4]dioxin-6-ylmethyl)-{2-[6-(6-methoxy[1,5]naphthyridin-4-yl)-[1,2,4]triazin-3-yl]ethyl}amine a) 3-[7-Fluoro-2,3-dihydro-benzo[1,4]dioxin-6-ylmethyl)-amino]propionic acid ethyl ester.

To a solution of β-alanine ethyl ester hydrochloride (0.45 g, 2.9 mmol), triethylamine (0.40 mL, 0.29 g, 2.9 mmol) and 7-fluoro-2,3-dihydro-benzo[1,4]dioxine-6-carbaldehyde (0.53 g, 2.9 mmol) in DMF (5.0 mL) was added molecular sieves (4A) at rt. After stirring at rt for 18 h, the reaction mixture was filtered, the solids washed with DMF and the filtrate concentrated under reduced pressure. The residue was purified by vacuum filtration through a pad of silica gel, eluting successively with 1%, 2% and 4% MeOH in CH$_2$Cl$_2$ and 90:10:1 CH$_2$Cl$_2$/MeOH/conc. aq. NH$_4$OH to afford the title compound as a clear oil; yield 0.58 g (71%): LC-MS (ES) 284 (M+H)$^+$.

b) 3-[(2,2-Dimethyl-propanoyl)-7-fluoro-2,3-dihydro-benzo[1,4]dioxin-6-ylmethyl)-amino]-propionic acid ethyl ester.

To a solution of 3-[7-fluoro-2,3-dihydrobenzo[1,4]dioxin-6-ylmethyl)-amino]-propionic acid ethyl ester (0.50 g, 1.8 mmol) in MeOH (10 mL) was added di-tert-butyl dicarbonate (0.46 g, 2.1 mmol) at rt. After stirring at RT for 18 h, the solvent was evaporated to afford the title compound sufficiently pure [LCMS (ES) m/e 384 (M+H)$^+$, 90%)] to use in step (c) without further purification.

c) N-(7-Fluoro-2,3-dihydro-benzo[1,4]dioxin-6-ylmethyl)-N-(2-hydrazinocarbonylethyl)-2,2-dimethyl-propionamide.

To a solution of crude 3-[(2,2-dimethyl-propanoyl)-7-fluoro-2,3-dihydro-benzo[1,4]dioxin-6-ylmethyl)-amino]-propionic acid ethyl ester (1.8 mmol maximum) in EtOH (5.0 mL) was added hydrazine hydrate (~55% hydrazine, 0.20 mL, 3.6 mmol). The reaction mixture was heated to reflux for 18 h. The solvent was evaporated and the residue purified by vacuum filtration through a pad of silica gel eluting successively with 2% and 4% MeOH in CH$_2$Cl$_2$ and 90:10:1 CH$_2$Cl$_2$/MeOH/conc. aq. NH$_4$OH to afford the title compound; yield 0.31 g (47%, 2-steps): LC-MS (ES) m/e 370 (M+H)$^+$.

d) N-(7-Fluoro-2,3-dihydrobenzo[1,4]dioxin-6-ylmethyl)-N-{2-[6-(6-methoxy-[1,5]naphthyridin-4-yl)-[1,2,4]triazin-3-ylethyl}-2,2-dimethyl-propionamide.

A solution of N-(7-fluoro-2,3-dihydro-benzo[1,4]dioxin-6-ylmethyl)-N-(2-hydrazinocarbonyl-ethyl)-2,2-dimethyl-propionamide (0.30 g, 0.78 mmol) and 2-bromo-1-(6-methoxy[1,5]naphthyridin-4-yl)ethanone (0.10 g, 0.36 mmol) in DMF (5.0 mL) was heated to 120° C. for 3 h. The solvent was removed under reduced pressure and the residue was purified by vacuum filtration through a pad of silica gel eluting successively with 1%, 2% and 4% MeOH in CH$_2$Cl$_2$ to afford the title compound as a yellow oil; yield 0.060 g (14%): LC-MS (ES) m/e 549 (M+H)$^+$.

e) (7-Fluoro-2,3-dihydrobenzo[1,4]dioxin-6-ylmethyl)-{2-[6-(6-methoxy-[1,5]naphthyridin-4-yl)-[1,2,4]triazin-3-yl]ethyl}amine.

To a solution of N-(7-fluoro-2,3-dihydrobenzo[1,4]dioxin-6-ylmethyl)-N-{2-[6-(6-methoxy-[1,5]naphthyridin-4-yl)-[1,2,4]triazin-2-yl-ethyl}-2,2-dimethyl-propionamide (0.060 g, 0.11 mmol) in CH$_2$Cl$_2$ (10 mL) was added TFA (1 mL). The reaction mixture was stirred at rt for 18 h. Volatile materials were removed under reduced pressure and the residue was purified by reverse-phase HPLC eluting with a gradient of 5-95% CH$_3$CN/H$_2$O. Fractions containing only desired product were concentrated. Trituration of the residue with ether afforded the TFA salt of the title compound as a yellow solid; yield 0.016 g (25%): $^1$H NMR (MeOH-d$_4$): δ 9.87 (s, 1H); 9.00 (d, 1H, J=4.6 Hz); 8.40 (d, 1H, J=9.2 Hz); 8.33 (d, 1H, J=4.6 Hz); 7.38 (d, 1H, J=9.1 Hz); 7.09 (d, 1H, J=7.2 Hz); 6.81 (d, 1H, J=10.6 Hz); 4.36 (s, 2H); 4.31 (d, 2H, J=4.9 Hz); 4.27 (d, 2H, J=5.5 Hz); 4.07 (s, 3H); 3.79-3.50 (m, 4H)

Example 16

Preparation of (2,3-dihydro[1,4]dioxino[2,3-c]pyridin-7-ylmethyl)(2-{5-[6-(methyloxy)-1,5-naphthyridin-4-yl]-2-pyridinyl}ethyl)amine (a) 1,1-dimethylethyl (2-{5-[6-(methyloxy)-1,5-naphthyridin-4-yl]-2-pyridinyl}ethyl)carbamate To a stirred solution of 1,1-trifluoromethanesulfonic acid 6-methoxy[1,5]naphthyridin-4-yl ester (2.0 g, 8.42 mmole)

in dry dioxane, (75 mL) at RT was added bis(pinacolato)diboron (2.14 g, 8.43 mmole), potassium acetate (1.91 g, 19.4 mmole), 1,1-bis(diphenylphosphino)ferrocene (0.18 g, 0.32 mmole) and [1,1'-bis(diphenylphosphino)ferrocene]dichloropalladium(II) complexed with dichloromethane (1:1) (0.26 g, 0.32 mmole). The reaction contents were heated to 80° C. for 24 h under nitrogen gas and then 1,1-bis(diphenylphosphino)ferrocene (0.18 g, 0.32 mmole), [1,1'-bis(diphenylphosphino)ferrocene]dichloropalladium(II) complexed with dichloromethane (1:1) (0.26 g, 0.32 mmole), potassium carbonate (2.68 g, 19.44 mmole) and 1,1-dimethylethyl [2-(5-bromo-2-pyridinyl)ethyl]carbamate (1.94 g, 6.48 mmole) were added to the reaction pot. After 24 h of vigorous stirring at 80° C., the reaction contents were filtered through a scinter-glass funnel containing a bed of celite (EtOAc). The filtrate was concentrated under vacuum and purified on silica (EtOAc) to afford the title compound (1.52 g, 62%) as a tan solid: LC-MS (ES) m/e 381 (M+H)⁺.

b) (2-{5-[6-(methyloxy)-1,5-naphthyridin-4-yl]-2-pyridinyl}ethyl)amine hydrochloride salt To a stirred solution of 1,1-dimethylethyl (2-(5-[6-(methyloxy)-1,5-naphthyridin-4-yl]-2-pyridinyl}ethyl)carbamate (4.0 mmole) in dry THF (20 mL) at RT was added 4 M HCl in dioxane (10 mL). After 4 h, the reaction suspension was concentrated in vacuo and dried under high vacuum to give the title compound (100%.) as an off-white solid: LC-MS (ES) m/e 281 (M+H)⁺.

c) (2,3-dihydro[1,4]dioxino[2,3-c]pyridin-7-ylmethyl)(2-{5-[6-(methyloxy)-1,5-naphthyridin-4-yl]-2-pyridinyl}ethyl)amine To a stirred solution of (2-{5-[6-(methyloxy)-1,5-naphthyridin-4-yl]-2-pyridinyl}ethyl)amine hydrochloride salt (0.69 mmole) in dry CH$_2$Cl$_2$ (25 mL) and dry EtOH (10 mL) at RT was added triethylamine (0.29 mL, 2.07 mmole) and 2,3-dihydro[1,4]dioxino[2,3-c]pyridine-7-carbaldehyde (0.12 g, 0.73 mmole). After 24 h, the reaction contents were concentrated and dried under high vacuum. To a stirred solution of the crude imine in dry EtOH (25 mL) at RT was added NaBH$_4$ (0.03 g, 0.73 mmole). After 24 h, Silica gel (5 g) was added to the reaction solution and the suspension was concentrated under vacuum to a dry solid. Purification on silica (CHCl$_3$/MeOH, 9:1 containing 5% NH$_4$OH) afforded the title compound (0.50 g, 72%) as light yellow solid: $^1$H NMR (400 MHz, CD$_3$OD) δ 9.52 (d, J=1.8 Hz, 1H), 9.22 (d, J=5.6 Hz, 1H), 9.02 (d, J=8.3 Hz; 1H), 8.57 (m, 2H), 8.48 (d, J=5.6 Hz, 1H), 8.19 (d, J=9.3 Hz, 1H), 7.79 (s, 1H), 7.68 (d, J=9.3 Hz, 1H), 4.66 (m, 4H), 4.54 (s, 2H), 4.13 (s, 3H), 3.82 (m, 2H), 3.71 (s, 2H). LC-MS (ES) m/e 430 (M+H)⁺.

Example 17

Preparation of (2,3-dihydro[1,4]dioxino[2,3-c]pyridin-7-ylmethyl)(2-{6-[6-(methyloxy)-1,5-naphthyridin-4-yl]-3-pyridinyl}ethyl)amine According to the procedure of Example 16, except substituting 1,1-dimethylethyl [2-(6-chloro-3-pyridinyl)ethyl]carbamate (1.0 g, 3.90 mmole) for 1,1-dimethylethyl [2-(5-bromo-2-pyridinyl)ethyl]carbamate, the title compound (0.16 g, 40% overall yield) was prepared as an off-white solid following flash chromatography on silica gel (CHCl$_3$/MeOH, 9:1, containing 5% NH$_4$OH): $^1$H NMR (400 MHz, CD$_3$OD) δ 9.17 (m, 2H), 8.75 (d, J=8.3 Hz, 1H), 8.66 (d, J=8.3 Hz, 1H), 8.49-8.54 (m, 3H), 7.76 (s, 1H), 7.56 (d, J=9.3 Hz, 1H), 4.67 (m, 2H), 4.63 (s, 2H), 4.53 (m, 2H), 4.14 (s, 3H), 3.70 (m, 2H), 3.51 (m, 2H). LC-MS (ES) m/e 430 (M+H)⁺.

Example 18

Preparation of N-(2-{5-[6-(methyloxy)-1,5-naphthyridin-4-yl]-2-pyridinyl}ethyl)-3-oxo-3,4-dihydro-2H-pyrido[3,2-b][1,4]thiazine-6-carboxamide To a stirred solution of (2-{5-[6-(methyloxy)-1,5-naphthyridin-4-yl]-2-pyridinyl}ethyl)amine hydrochloride salt (1.08 mmole) in DMF (25 mL) at RT was added diisopropylethylamine (0.75 mL, 4.32 mmole), 3-oxo-3,4-dihydro-2H-pyrido[3,2-b][1,4]thiazine-6-carboxylic acid (0.23 g, 1.08 mmole), hydroxybenzotriazole hydrate (0.16 g, 1.19 mmole) and EDC (0.23 g, 1.19 mmole). After 18 h, the reaction contents were concentrated and dried under high vacuum. Purification on silica (CHCl$_3$/MeOH, 9:1 containing 5% NH$_4$OH) afforded the title compound (0.40 g, 79%) as light yellow solid: $^1$H NMR (400 MHz, CD$_3$OD) δ 9.55 (m, 1H), 9.19 (m, 1H), 9.09 (d, J=8.3 Hz, 1H), 8.53 (d, J=9.2 Hz, 1H), 8.42 (m, 1H), 8.23 (d, J=7.7 Hz, 1H), 7.88 (d, J=8.3 Hz, 1H), 7.61 (m, 2H), 4.5 (s, 3H), 4.02 (m, 2H), 3.62 (m, 2H), 3.54 (m, 2H). LC-MS (ES) m/e 473 (M+H)⁺.

Example 19

Preparation of N-(2-{6-[6-(methyloxy)-1,5-naphthyridin-4-yl]-3-pyridinyl}ethyl)-3-oxo-3,4-dihydro-2H-pyrido[3,2-b][1,4]thiazine-6-carboxamide According to the procedure of Example 18, except substituting (2-{6-[6-(methyloxy)-1,5-naphthyridin-4-yl]-3-pyridinyl}ethyl)amine hydrochloride salt (0.89 mmole) for (2-{5-[6-(methyloxy)-1,5-naphthyridin-4-yl]-2-pyridinyl}ethyl)amine hydrochloride salt, the title compound (0.31 g, 75% yield) was prepared as an off-white solid following flash chromatography on silica gel (CHCl$_3$/MeOH, 9:1, containing 5% NH$_4$OH): $^1$H NMR (400 MHz, CD$_3$OD) δ 9.05 (m, 2H), 8.61 (m, 2H), 8.46 (d, J=9.1 Hz, 1H), 8.31 (m, 1H), 7.88 (d, J=7.3 Hz, 1H), 7.65 (m, 1H), 7.48 (d, J=9.1 Hz, 1H), (s, 3H), 3.87 (m, 2H), 3.79 (m, 2H), 3.24 (m, 2H). LC-MS (ES) m/e 473 (M+H)⁺.

The invention claimed is:

1. A compound selected from compounds of formula (I):

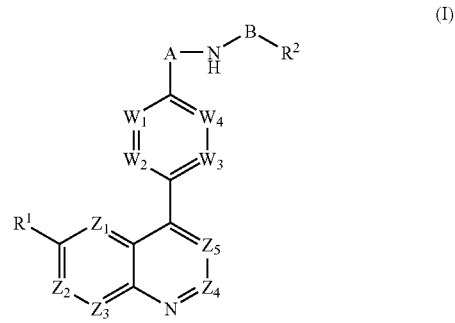

and pharmaceutically acceptable salts thereof; wherein:
one of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;
$R^1$ and $R^{1a}$ are independently hydrogen; hydroxy; $(C_{1-6})$alkoxy unsubstituted or substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, CONH$_2$, hydroxy, ($C_{1-6}$)alkylthio, heterocyclylthio, heterocyclyloxy, arylthio, aryloxy, acylthio, acyloxy or ($C_{1-6}$)alkylsulphonyloxy; ($C_{1-6}$)alkoxy-substituted($C_{1-6}$)alkyl; halogen; ($C_{1-6}$)alkyl; ($C_{1-6}$)alkylthio; trifluoromethyl; trifluoromethoxy; nitro; cyano; azido; acyl; acyloxy; acylthio; ($C_{1-6}$)alkylsulphonyl; ($C_{1-6}$)alkylsulphoxide; arylsulphonyl; arylsulphoxide or an amino, piperidyl, guanidino or amidino group optionally N-substituted by one or two ($C_{1-6}$)alkyl, acyl or ($C_{1-6}$)alkylsulphonyl groups;

provided that when $Z_1$, $Z_2$, $Z_3$, $Z_4$ and $Z_5$ are $CR^{1a}$ or CH, then $R^1$ is not hydrogen;

$W_1$, $W_2$, $W_3$ and $W_4$ are each independently selected from N or $CR^3$;

each $R^3$ is independently selected from:

hydrogen; hydroxy; halogen; trifluoromethyl; trifluoromethoxy; cyano; nitro; azido; acyl; acyloxy; acylthio; amino, mono- and di-($C_{1-6}$)alkylamino; and substituted and unsubstituted ($C_{1-6}$)alkoxy, ($C_{1-6}$)alkyl, ($C_{3-7}$)cycloalkyl, aminocarbonyl, ($C_{1-6}$)alkylthio, ($C_{1-6}$)alkylsulphonyl, and ($C_{1-6}$)alkylsulphoxide;

A is $(CRR)_n$;
B is $(CRR)_m$, C=O, or $SO_2$;
n is 1 or 2;
m is 1 or 2
provided that when n is 1, m is 2; when n is 2, m is 1; and when B is C=O or $SO_2$ then n is 2;
each R is independently selected from
hydrogen; halogen; trifluoromethyl; trifluoromethoxy; cyano; nitro; azido; acyl; acyloxy; acylthio; amino, mono- and di-($C_{1-6}$)alkylamino; and substituted and unsubstituted ($C_{1-6}$)alkoxy, ($C_{1-6}$)alkyl, ($C_{3-7}$)cycloalkyl, aminocarbonyl, ($C_{1-6}$)alkylthio, ($C_{1-6}$)alkylsulphonyl, and ($C_{1-6}$)alkylsulphoxide;

$R^2$ is a group:

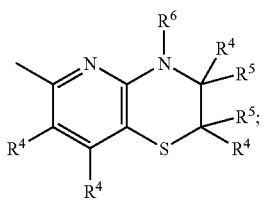

each $R^4$ and $R^5$ is independently selected from: hydrogen; ($C_{1-4}$)alkylthio; halo; carboxy($C_{1-4}$)alkyl; halo($C_{1-4}$)alkoxy; halo($C_{1-4}$)alkyl; ($C_{1-4}$)alkyl; ($C_{1-4}$)alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$)alkylcarbonyloxy; ($C_{1-4}$)alkoxycarbonyl ($C_{1-4}$)alkyl; hydroxy; hydroxy($C_{1-4}$)alkyl; mercapto($C_{1-4}$)alkyl; ($C_{1-4}$)alkoxy; nitro; cyano; carboxy; amino or aminocarbonyl optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)alkyl or ($C_{2-4}$)alkenyl; ($C_{2-6}$)alkenyl; ($C_{1-4}$)alkylsulphonyl; ($C_{2-4}$)alkenylsulphonyl; aminosulphonyl wherein the amino group is optionally mono- or di-substituted by ($C_{1-4}$)alkyl or ($C_{2-4}$)alkenyl; aryl; aryl ($C_{1-4}$)alkyl; and aryl($C_{1-4}$)alkoxy; or $R^4$ and $R^5$ may together represent oxo;

$R^6$ is hydrogen; trifluoromethyl; ($C_{1-4}$)alkyl unsubstituted or substituted by hydroxy, ($C_{1-6}$)alkoxy, ($C_{1-6}$)alkylthio, halo or trifluoromethyl; ($C_{2-4}$)alkenyl; aryl; aryl($C_{1-4}$) alkyl; arylcarbonyl; heteroarylcarbonyl; ($C_{1-4}$)alkoxycarbonyl; ($C_{1-4}$)alkylcarbonyl; formyl; ($C_{1-6}$) alkylsulphonyl; or aminocarbonyl wherein the amino group is optionally substituted by ($C_{1-4}$)alkoxycarbonyl, ($C_{1-4}$) alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$) alkyl or ($C_{2-4}$)alkenyl; and "acyl" is a formyl or a ($C_{1-6}$)alkylcarbonyl group.

2. A compound according to claim 1 wherein $Z_5$ is CH or N, $Z_3$ is CH or CF and $Z_1$, $Z_2$ and $Z_4$ are each CH, or $Z_1$ is N, $Z_3$, is CH or CF and $Z_2$, $Z_4$ and $Z_5$ are each CH.

3. A compound according to claim 1 wherein $R^1$ is methoxy and $R^{1a}$ is H or when $Z_3$ is $CR^{1a}$ it may be C—F.

4. The compound according to claim 1 wherein:
a) $W_1$-$W_4$ are independently $CR^3$;
b) $W_1$, $W_3$ and $W_4$ are N and W2 is $CR^3$;
c) $W_2$ is N and $W_1$, $W_3$ and $W_4$ are independently $CR^3$;
d) $W_3$ is N and $W_1$, $W_2$ and $W_4$ are independently $CR^3$; or
e) $W_4$ is N and $W_1$-$W_3$ are independently $CR^3$.

5. A compound according to claim 1 wherein $R^3$ is independently selected from hydrogen, substituted and unsubstituted ($C_{1-6}$)alkoxy, and $NH_2$.

6. A compound according to claim 1 wherein R is independently selected from hydrogen, substituted and unsubstituted ($C_{1-6}$)alkyl, $CONH_2$, COOH, hydroxy, halogen, and substituted and unsubstituted ($C_{1-6}$)alkoxy.

7. The compound according to claim 1 wherein $R^4$ and $R^5$ are independently selected from hydrogen, halo, hydroxy, ($C_{1-4}$)alkoxy, trifluoromethoxy, nitro, cyano, aryl($C_{1-4}$) alkoxy and ($C_{1-4}$)alkylsulphonyl, and $R^6$ is H or ($C_{1-4}$)alkyl.

8. The compound according to claim 7 wherein each $R^4$ is independently selected from hydrogen, chloro, fluoro, hydroxy, methoxy, trifluoromethoxy, benzyloxy, nitro, cyano and methylsulphonyl, and $R^5$ and $R^6$ are hydrogen.

9. The compound according to claim 8 wherein $R^4$ is independently hydrogen, fluorine or nitro.

10. The compound according to claim 9 wherein $R^4$ is hydrogen.

11. The compound according to claim 1 wherein $R^2$ is a group:

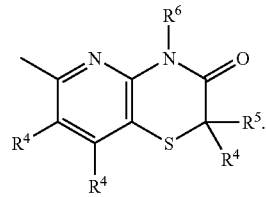

12. The compound according to claim 11 wherein $R^4$ and $R^5$ are independently selected from hydrogen, halo, hydroxy, ($C_{1-4}$)alkoxy, trifluoromethoxy, nitro, cyano, aryl($C_{1-4}$) alkoxy and ($C_{1-4}$)alkylsulphonyl, and $R^6$ is H or ($C_{1-4}$)alkyl.

13. The compound according to claim 12 wherein each $R^4$ is independently selected from hydrogen, chloro, fluoro, hydroxy, methoxy, trifluoromethoxy, benzyloxy, nitro, cyano and methylsulphonyl, and $R^5$ and $R^6$ are hydrogen.

14. The compound according to claim 13 wherein $R^4$ is independently hydrogen, fluorine or nitro.

15. The compound according to claim 14 wherein $R^4$ is hydrogen.

16. A compound selected from the following compounds and pharmaceutically acceptable salts thereof:
- 6-({2-[4-(6-Methoxy-[1,5]naphthyridin-4-yl)phenyl]ethylamino}methyl)-4H-pyrido[3,2-b][1,4]thiazin-3-one;
- 6-({2-[4-(6,8-difluoroquinolin-4-yl)phenyl]ethylamino}methyl)-4H-pyrido[3,2-b][1,4]thiazin-3-one;
- 6-({2-[4-(8-Fluoro-6-methoxyquinolin-4-yl)phenyl]ethylamino}methyl)-4H-pyrido[3,2-b][1,4]thiazin-3-one;
- 6-({2-[6-(6-methoxy-[1,5]naphthyridin-4-yl)pyridin-3-yl]ethylamino}methyl)-4H-pyrido[3,2-b][1,4]thiazin-3-one;
- 6-({2-[5-(6-methoxy-[1,5]naphthyridin-4-yl)pyridin-2-yl]ethylamino}methyl)-4H-pyrido[3,2-b][1,4]thiazin-3-one;
- N-(2-{6-[6-(methyloxy)-1,5-naphthyridin-4-yl]-3-pyridinyl}ethyl)-3-oxo-3,4-dihydro-2H-pyrido[3,2-b][1,4]thiazine-6-carboxamide;
- N-(2-{5-[6-(methyloxy)-1,5-naphthyridin-4-yl]-2-pyridinyl}ethyl)-3-oxo-3,4-dihydro-2H-pyrido[3,2-b][1,4]thiazine-6-carboxamide.

17. The compound according to claim 1 wherein:
$Z_5$ is CH or N, $Z_3$ is CH or CF and $Z_1$, $Z_2$ and $Z_4$ are each CH; or $Z_1$ is N, $Z_3$ is CH or CF and $Z_2$, $Z_4$ and $Z_5$ are each CH;
$R^1$ is methoxy, amino($C_{3-5}$)alkyloxy, guanidino($C_{3-5}$)alkyloxy, piperidyl($C_{3-5}$)alkyloxy, nitro or fluoro;
$W_1$-$W_4$ are independently $CR^3$; or
$W_1$, $W_3$ and $W_4$ are N and $W_2$ is $CR^3$; or
$W_2$ is N and $W_1$, $W_3$ and $W_4$ are independently $CR^3$; or
$W_3$ is N and $W_1$, $W_2$ and $W_4$ are independently $CR^3$; or
$W_4$ is N and $W_1$-$W_3$ are independently $CR^3$;
$R^3$ is independently selected from hydrogen, ($C_{1-6}$)alkoxy, and $NH_2$; and
R is independently selected from hydrogen, ($C_{1-6}$)alkyl, $CONH_2$, COOH, hydroxy, halogen, and ($C_{1-6}$)alkoxy.

18. The compound according to claim 17 wherein $R^4$ and $R^5$ are independently selected from hydrogen, halo, hydroxy, ($C_{1-4}$)alkoxy, trifluoromethoxy, nitro, cyano, aryl($C_{1-4}$)alkoxy and ($C_{1-4}$)alkylsulphonyl; and $R^6$ is H or ($C_{1-4}$)alkyl.

19. The compound according to claim 17 wherein $R^2$ is a group:

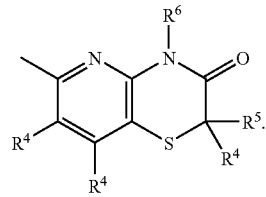

wherein $R^4$ and $R^5$ are independently selected from hydrogen, halo, hydroxy, ($C_{1-4}$)alkoxy, trifluoromethoxy, nitro, cyano, aryl($C_{1-4}$)alkoxy and ($C_{1-4}$)alkylsulphonyl; and $R^6$ is hydrogen or ($C_{1-4}$)alkyl.

20. The compound according to claim 1 wherein:
$Z_1$, $Z_2$, $Z_4$ and $Z_5$ are each CH and $Z_3$ is CH or CF, or
$Z_1$ is N and $Z_2$, $Z_3$, $Z_4$ and $Z_5$ are each CH;
$R^1$ is methoxy or fluoro;
$W_1$-$W_4$ are independently CH; or
$W_1$, $W_3$ and $W_4$ are N and $W_2$ is CH; or
$W_2$ is N and $W_1$, $W_3$ and $W_4$ are independently CH; or
$W_3$ is N and $W_2$ and $W_4$ are independently CH; or
$W_4$ is N and $W_1$-$W_3$ are independently CH;
R is hydrogen;
$R_2$ is a group:

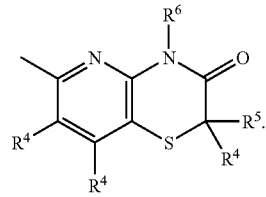

and $R^4$, $R^5$ and $R^6$ are hydrogen.

21. A pharmaceutical composition comprising the compound according to claim 1 and a pharmaceutically acceptable carrier.

22. A pharmaceutical composition comprising the compound according to claim 16 and a pharmaceutically acceptable carrier.

23. A pharmaceutical composition comprising the compound according to claim 20 and a pharmaceutically acceptable carrier.

* * * * *

UNITED STATES PATENT AND TRADEMARK OFFICE
CERTIFICATE OF CORRECTION

PATENT NO. : 7,618,959 B2
APPLICATION NO. : 10/533501
DATED : November 17, 2009
INVENTOR(S) : Axten et al.

It is certified that error appears in the above-identified patent and that said Letters Patent is hereby corrected as shown below:

Title Page Item (73) should read

(73) Assignee: Glaxo Group Limited
Brentford, Middlesex, United Kingdom

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,618,959 B2 | Page 1 of 1 |
| APPLICATION NO. | : 10/533501 | |
| DATED | : November 17, 2009 | |
| INVENTOR(S) | : Axten et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 565 days Delete the phrase "by 565 days" and insert -- by 969 days --

Signed and Sealed this

Seventeenth Day of August, 2010

David J. Kappos
*Director of the United States Patent and Trademark Office*